US008801772B2

(12) United States Patent
Shobayashi et al.

(10) Patent No.: US 8,801,772 B2
(45) Date of Patent: Aug. 12, 2014

(54) STENT TO BE USED IN TUBULAR ORGAN IN VIVO

(75) Inventors: Yasuhiro Shobayashi, Kanagawa (JP); Kazuo Tanishita, Kanagawa (JP); Satoshi Tateshima, Tokyo (JP)

(73) Assignee: Keio University, Tokyo (JP)

( * ) Notice: Subject to any disclaimer, the term of this patent is extended or adjusted under 35 U.S.C. 154(b) by 168 days.

(21) Appl. No.: 13/148,212

(22) PCT Filed: Feb. 5, 2010

(86) PCT No.: PCT/JP2010/052115
§ 371 (c)(1),
(2), (4) Date: Aug. 5, 2011

(87) PCT Pub. No.: WO2010/090348
PCT Pub. Date: Aug. 12, 2010

(65) Prior Publication Data

US 2012/0041540 A1 Feb. 16, 2012

(30) Foreign Application Priority Data

Feb. 6, 2009 (JP) ................................ 2009-026475

(51) Int. Cl.
*A61F 2/86* (2013.01)

(52) U.S. Cl.
USPC ........................................ 623/1.15; 623/1.51

(58) Field of Classification Search
USPC ............ 623/1.1, 1.11, 1.12, 1.13, 1.15, 1.16, 623/1.17, 1.22, 1.32, 1.33, 1.34, 1.49–1.54
See application file for complete search history.

(56) References Cited

U.S. PATENT DOCUMENTS

| | | | | |
|---|---|---|---|---|
| 5,951,599 | A | 9/1999 | McCrory | |
| 6,976,993 | B2 | 12/2005 | Schaldach et al. | |
| 2002/0193862 | A1 | 12/2002 | Mitelberg et al. | |
| 2003/0004567 | A1 * | 1/2003 | Boyle et al. | 623/1.16 |
| 2003/0105517 | A1 * | 6/2003 | White et al. | 623/1.17 |

(Continued)

FOREIGN PATENT DOCUMENTS

| | | |
|---|---|---|
| JP | 2001 509412 | 7/2001 |
| JP | 2003 93518 | 4/2003 |
| JP | 2005 534396 | 11/2005 |
| WO | 2009 105176 | 8/2009 |

OTHER PUBLICATIONS

International Search Report issued May 18, 2010 in PCT/JP10/052115 filed Feb. 5, 2010.

*Primary Examiner* — David Isabella
*Assistant Examiner* — Suba Ganesan
(74) *Attorney, Agent, or Firm* — Oblon, Spivak, McClelland, Maier & Neustadt, L.L.P.

(57) ABSTRACT

Provided is a stent to be inserted into an in vivo organ having a tubular structure that allows a degree of freedom in design and excellent mechanical flexibility. A cylinder-shaped stent is inserted to be placed and used in the inner cavity of an in vivo tubular organ, wherein: the wall of the stent has a planar mesh pattern filled with a plurality of closed cells being adjacent to each other and having congruent shapes; the closed cells have point-symmetric parallel hexagonal shapes; all closed cells circumferentially adjacent to each other are congruent and similar in shape; two closed cells adjacent to each other sharing different sides form a substantially V-shaped member; and the vertex of each folded part in the substantially V-shaped member points to the circumferential direction.

10 Claims, 33 Drawing Sheets

(56) References Cited

U.S. PATENT DOCUMENTS

2003/0195616 A1* 10/2003 Pinchasik et al. ............ 623/1.16
2006/0129227 A1 6/2006 Hengelmolen
2007/0203564 A1* 8/2007 Rusk et al. ................... 623/1.13

* cited by examiner

A
B
C
b
$\frac{b}{\pi D} = 0.07$
$\frac{b}{\pi D} = 0.11$
$\frac{b}{\pi D} = 0.25$
L
$\pi D$
p1 (x1,y1)
p2 (x2,y2)
p3 (x3,y3)
p4 (x4,y4)
p5 (x5,y5)
p6 (x6,y6)

Pattern 0 Pattern A Pattern B

Pattern A

Pattern B

Fig. 9

| Values for (h), (l), and (b) of stent models | | | | | |
|---|---|---|---|---|---|
| | model | *L* (mm) | *πD* (mm) | *h* (mm) | *l* (mm) |
| Patten A | model 1 | 20 | 15.7 | 3.40 | 3.08 |
| | model 2 | 20 | 15.7 | 3.40 | 3.08 |
| | model 3 | 20 | 15.7 | 3.40 | 3.08 |
| Patten B | model 4 | 20 | 15.7 | 1.96 | 3.79 |
| | model 5 | 20 | 15.7 | 1.96 | 3.79 |
| | model 6 | 20 | 15.7 | 1.96 | 3.79 |

Fig. 10

| Finite element meshes of stent models for simulation | | | |
|---|---|---|---|
| | model | Node | Elements |
| Patten A | model 1 | 124445 | 54327 |
| | model 2 | 122291 | 51282 |
| | model 3 | 136277 | 60030 |
| Patten B | model 4 | 144795 | 62706 |
| | model 5 | 163500 | 72623 |
| | model 6 | 195133 | 82455 |

Sectional view showing a compressed stent model.

A

B

A

B

A

B

A

B

A

B

STENT TO BE USED IN TUBULAR ORGAN IN VIVO

TECHNICAL FIELD

The present invention relates to a stent inserted to be placed and used in the inner cavity of an in vivo tubular organ.

BACKGROUND OF THE INVENTION

Cylindrical stents to be inserted to be placed for use in in vivo organs having tubular structures (e.g., blood vessels, esophagus, and trachea) are used in order to expand or maintain tubular structures for treatment of aneurysm, thrombosis, or the like.

Most in vivo tubular structures are complex such as in the cases of bending structures. Hence, the insertion of a stent into a site having such a complicated structure requires mechanical flexibility.

For example, a brain aneurysm is a type of aneurysmal vascular lesion that is generated on the arterial wall of a cerebral blood vessel. A brain aneurysm rupture causes the onset of cerebral hemorrhages such as subarachnoid hemorrhages that result in high mortality rates. Stents are also used in intravascular operations for such brain aneurysms. Among in vivo organs having tubular structures, the cerebrovascular system has a particularly complicated structure, in which many sites characterized by a large degree of curvature are present. When a stent is inserted into such a site, the stent is required to have a particularly high degree of mechanical flexibility.

A stent is generally formed of biocompatible metal wires that form a specific mesh pattern (network structure). There are mesh patterns having open cell structures, wherein mesh-composing cells (openings) and adjacent cells do not share some sides or vertices and mesh patterns having closed cell structures, wherein mesh-composing cells (openings) and adjacent cells share all sides and vertices. Stents having open cell structures have a high degree of flexibility because of their structures and thus are useful. An example thereof is a Neuroform Stent (Neuroform Micro delivery Stent System, Boston Scientific/, Fremont, Calif.) (see Sepehr Sani. Et al., Nurosurg Focus 18 (2): E4, 2005, p. 1-5). However, concerns have been raised that in a stent having an open cell structure, some wires (struts) may protrude outside the stent when it is bent, so as to injure in vivo tubular tissue such as the tissue of a blood vessel into which the stent has been inserted to be placed.

On the other hand, concerns that some wires (struts) may protrude outside the stent have not been raised for a stent having a closed cell structure (see JP Patent Publication (Kokai) No. 2003-93518 A, JP Patent Publication (Kokai) No. 2003-93519 A, and Randall T. Higashida et al., AJNR Am J Neuroradiol 26: 1751-1756, August 2005, p. 1751-1756). However, stents having closed cell structures may have poor flexibility because of their structures. Hence, there has been doubt about the usefulness of such a stent for the cerebrovascular system, which requires a particularly flexible stent. However, the relationship between a mesh pattern having a closed cell structure and flexibility has not yet been analyzed.

DISCLOSURE OF THE INVENTION

An object of the present invention is to provide a stent to be inserted to be placed for use in the inner cavity of an in vivo tubular organ that has a degree of freedom in design and excellent mechanical flexibility.

The present inventors have intensively examined the structures of stents having closed cell structures (and thus having good flexibility) that can be safely used for in vivo organs having cyclic structures without allowing some wires (struts) to protrude outside the stent. The present inventors have conducted structural analysis for stents having closed cell structures and various mesh patterns using a finite element method. In addition, the present inventors have actually produced such stents and verified the validity of the structural analysis thereof.

As a result, the present inventors have discovered a mesh pattern that can allow a degree of freedom in stent design and imparts flexibility to stents, and thus they have completed the present invention.

Furthermore, the present inventors have discovered the following: a tubular stent having the above mesh pattern can be braided with wires, so that the prevention of blood flow into a mass such as an aneurysm or varix while retaining the flexibility of the stent and the prevention of the rupture of such a mass can be expected, for example.

Specifically, the present invention is as follows.

[1] A cylinder-shaped stent to be inserted to be placed and used in the inner cavity of an in vivo tubular organ, wherein:
- the wall of the stent has a planar mesh pattern filled with a plurality of closed cells being adjacent to each other and having congruent shapes;
- the closed cells have point-symmetric parallel hexagonal shapes;
- all closed cells circumferentially adjacent to each other are congruent and similar in shape;
- two closed cells adjacent to each other sharing different sides form a substantially V-shaped member; and
- the vertex of the folded part of the substantially V-shaped member points to the circumferential direction.

[2] The stent according to [1], which is a cylinder-shaped stent to be inserted to be placed and used in the inner cavity of an in vivo tubular organ, wherein:
- the wall of the stent has a planar mesh pattern filled with a plurality of closed cells being adjacent to each other and having congruent shapes;
- the closed cells have point-symmetric substantially concave and substantially parallel hexagonal shapes; and
- the interior angles at two out of six vertices, between which two other vertices are located, are each greater than 180°.

[3] The cylinder-shaped stent to be inserted to be placed and used in the inner cavity of an in vivo tubular organ, wherein:
- the wall of the stent has a planar mesh pattern filled with a plurality of closed cells being adjacent to each other and having congruent shapes;
- the closed cells have point-symmetric substantially concave and substantially parallel hexagonal shapes; and
- the interior angles at two out of six vertices, between which two other vertices are located, are each greater than 180°.

[4] The stent according to [2] or [3], which is a cylinder-shaped stent to be inserted to be placed and used in the inner cavity of an in vivo tubular organ, wherein:
- the wall of the stent has a planar mesh pattern filled with a plurality of closed cells being adjacent to each other and having congruent shapes;
- the closed cells have point-symmetric substantially-concave hexagonal shapes; and
- when substantially concave hexagon P is represented by p1, p2, p3, p4, p5, and p6, side p1p2 (side 1) and side p4p5 (side 1) are substantially the same in length and substantially parallel to each other, side p2p3 (side 2) and side p5p6 (side 2) are substantially the same in length and substantially parallel to each other, side p3p4 (side 3) and side p6p1 (side 3) are substantially the same in length and substantially parallel to each other, and the interior angles at vertex p1 and vertex p4 are each greater than 180°, and when a flatly developed plan view of the stent is superimposed on an xy coordinate grid so that vertex p3 located between side p2p3 (side 2) and side p3p4 (side 3) or vertex p6 located between side p5p6 (side 2) and side p6p1 (side 3) of a plurality of closed cells circumferentially adjacent to each other in the flatly developed plan view of the stent is present on the y axis of the xy coordinate grid, the coordinates of vertices p1, p2, p3, p4, p5, and p6 are determined to be (x1, y1), (x2, y2), (x3, y3), (x4, y4), (x5, y5), and (x6, y6), respectively, the absolute value of distance x1-x4 between vertices p1 and p4 on the x-axis is determined to be "b," and the outer diameter of the stent is denoted by "D," b/πD ranges from 0.10 to 0.5.

[5] The stent according to [2] or [3], which is a cylinder-shaped stent to be inserted to be placed and used in the inner cavity of an in vivo tubular organ, wherein:

the wall of the stent has a planar mesh pattern filled with a plurality of closed cells being adjacent to each other and having congruent shapes and a flatly developed plan view of the stent is shown in FIG. 1A; and when the outer diameter of the stent is denoted by "D," and the circumferential distance in the stent between vertex p6 and vertex p3 that are each located between side 2 and side 3 of a single closed cell unit shown in FIG. 3 is denoted by "b," b/πD ranges from 0.10 to 0.5.

[6] The stent according to any one of [2] to [5], wherein some of the 6 sides of each closed cell having a substantially concave hexagonal shape are arc-like.

[7] The stent according to [4], wherein side p2p3 (side 2), side p3p4 (side 3), side p5p6 (side 2), and side p6p1 (side 3) are arc-like.

[8] The stent according to any one of [1] to [7], which is formed using titanium, nickel, stainless steel, platinum, gold, silver, copper, iron, chromium, cobalt, aluminium, molybdenum, manganese, tantalum, tungsten, niobium, magnesium, calcium, an alloy containing any thereof, or a synthetic resin as a material.

[9] The stent according to [8], which is formed using a biodegradable polymer as a material.

[10] The stent according to any one of [1] to [9], wherein stent strut portions forming the cells of the stent are slidably braided with wires without fixing the wires to the stent, so as to enhance the function of interrupting blood flow while retaining flexibility.

[11] The stent according to [10], wherein:

a plurality of wires and stent struts are braided so that the wires alternately cross the stent struts; and a stent portion near the center of the stent accounting for a third (⅓) or more the longitudinal length of the stent is braided with wires.

[12] The stent according to any one of [1] to [11], which carries an agent so that the agent can be eluted.

[13] The stent according to [12], wherein the agent is selected from the group consisting of an intimal-thickening suppressing agent, an anticancer agent, an immunosuppressive agent, an antibiotic, an antirheumatic drug, an antithrombotic drug, an HMG-CoA reductase inhibitor, an ACE inhibitor, a calcium antagonist, an antihyperlipidemic agent, an antiinflammatory agent, an integrin inhibitor, an antiallergic agent, an antioxidant, a GPIIbIIIa antagonist, retinoid, flavonoid, carotenoid, a lipid improving drug, a DNA synthesis inhibitor, a tyrosine kinase inhibitor, an anti-platelet agent, a vascular smooth muscle growth inhibitor, an antiinflammatory drug, and interferon.

[14] The stent according to any one of [1] to [13], wherein the in vivo tubular organ is selected from the group consisting of a blood vessel, the trachea, the esophagus, the large intestines, the small intestines, the duodenum, urinary tracts, the urethra, and bile ducts.

[15] The stent according to [14], wherein the in vivo tubular organ is a cerebral blood vessel.

The description includes part or all of the contents as disclosed in the description and/or drawings of Japanese Patent Application No. 2009-026475, which is a priority document of the present application.

BRIEF DESCRIPTION OF THE DRAWINGS

FIG. 1A shows a tessellation (tiling) of closed cells (a planform in which closed cells are filled). FIG. 1B shows a projection drawing of the cylindrical stent. FIG. 1C shows a photograph of the cylindrical stent.

FIG. 2C shows a mesh pattern wherein some sides of a closed cell are arc-like.

closed cells are convex hexagons (in which all interior angles are each less than 180°) (FIG. 5A);

closed cells are concave hexagons with interior angles of greater than 180°, wherein each interior angle is slightly greater than 180° (FIG. 5B); or closed cells are concave hexagons with interior angles of greater than 180°, wherein each interior angle is far greater than 180° (FIG. 5C).

Figure 6:
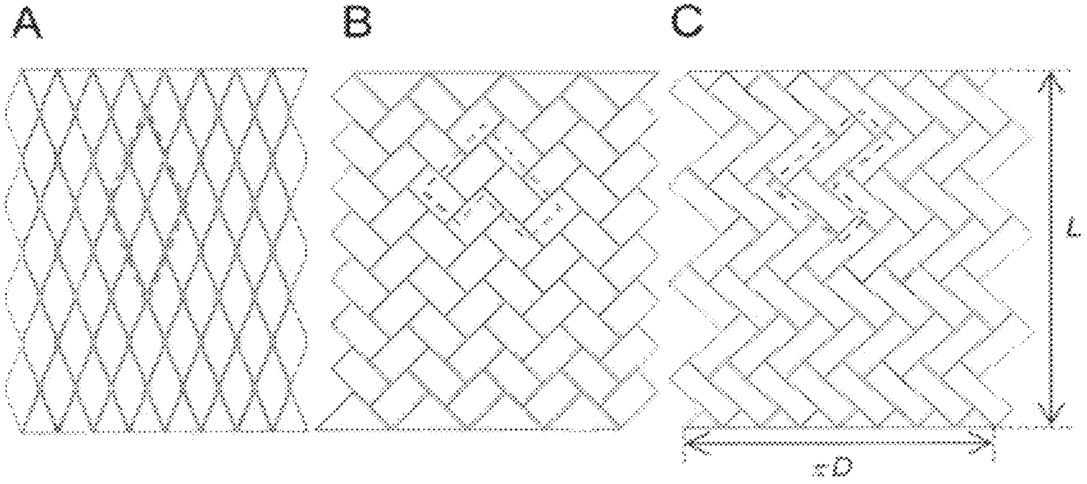

FIG. 6 shows mesh patterns of the 3 types of closed cell structure examined. FIG. 6A shows a diamond type (pattern 0), FIG. 6B shows an arrow-tip type (pattern A), and FIG. 6C shows an arrow-tip type rotated by 90° (pattern B).

Figure 7:
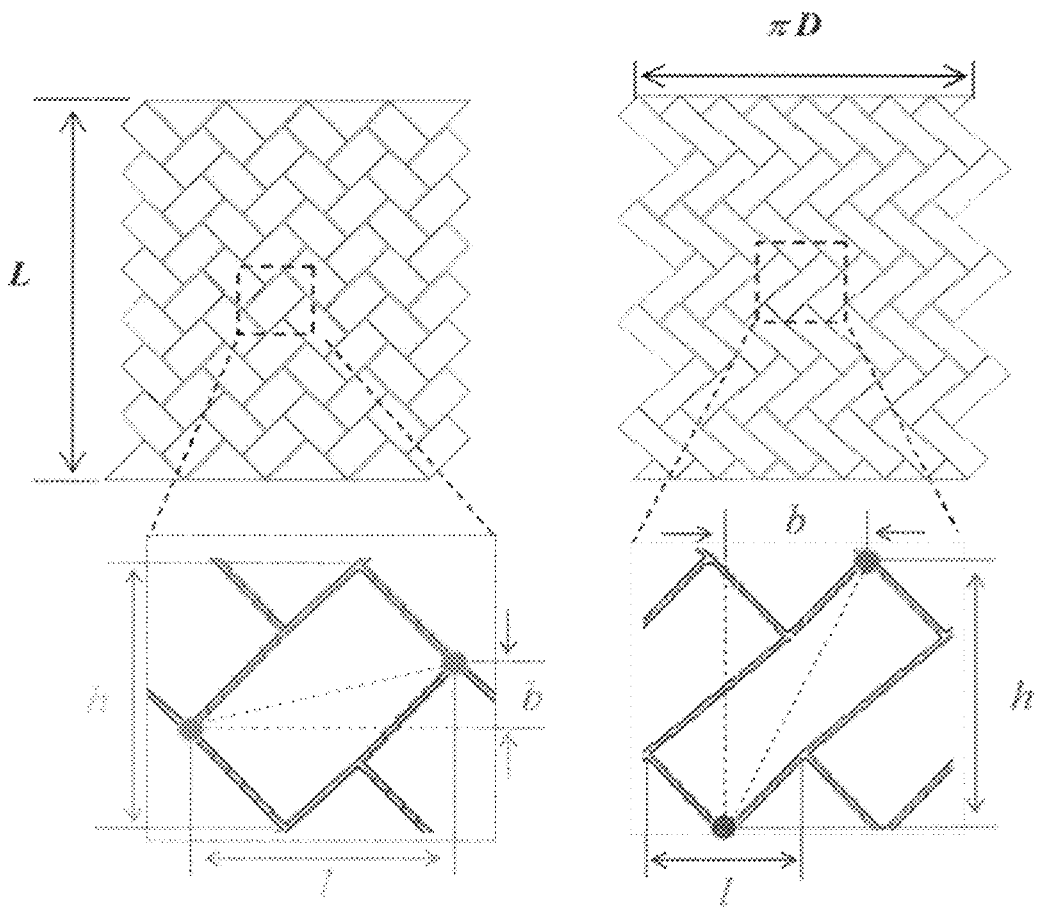

FIG. 7 shows pattern A and pattern B (shown in FIG. 6) in more detail.

Figure 8A:
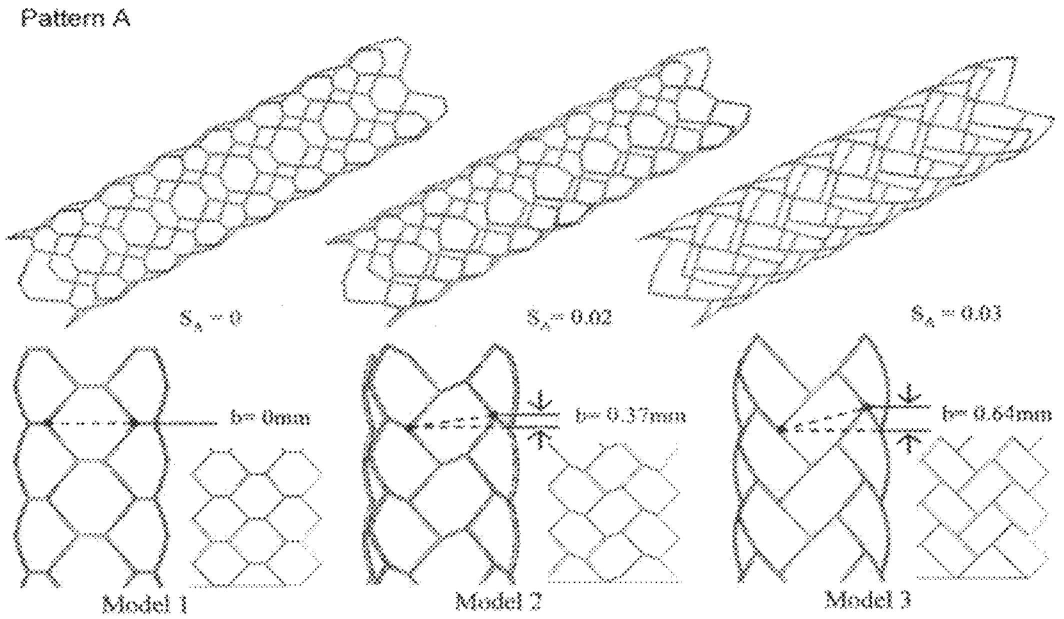

FIG. 8A shows the structures of 3 stent models of pattern A shown in FIG. 6.

Figure 8B:
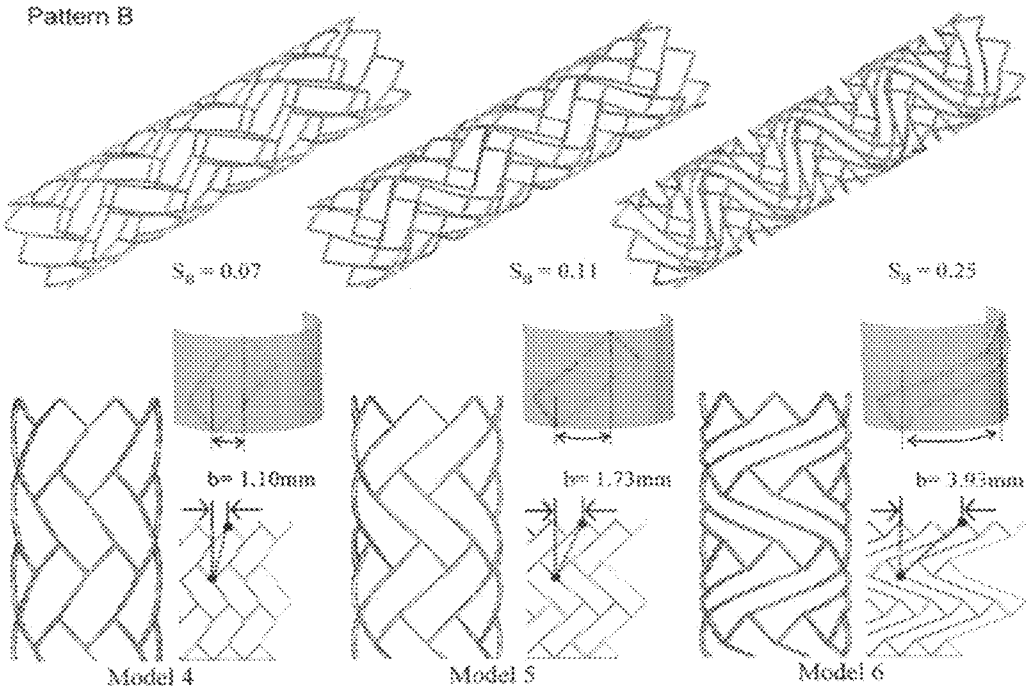

FIG. 8B shows the structures of 3 stent models of pattern B shown in FIG. 6.

FIG. 9 shows the structural parameters of stent models.

FIG. 10 shows the finite element models of stents in more detail.

Figure 11:
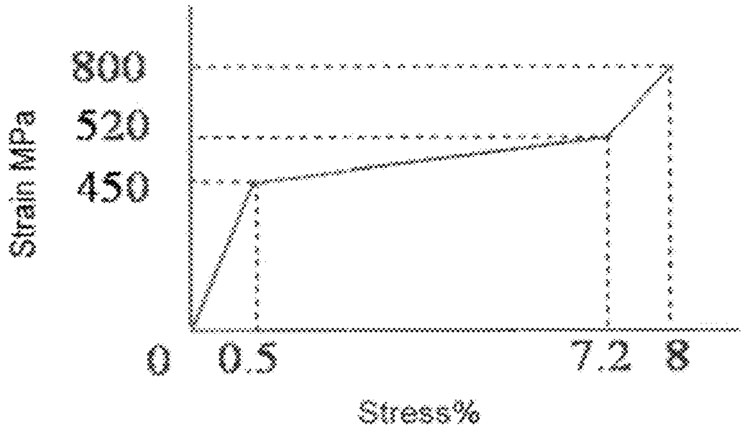

FIG. 11 shows an assumed stress-strain curve for an Ni—Ti alloy composed of Ti-55.9 wt % Ni.

Figure 12:
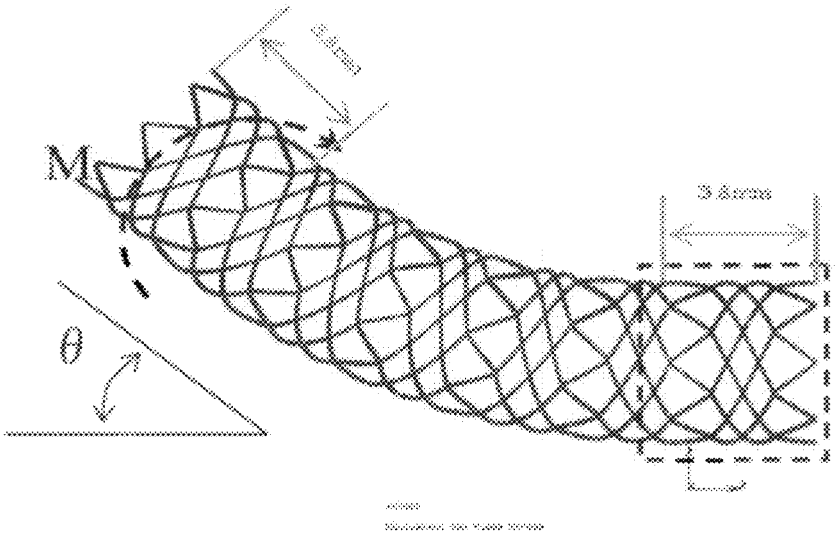

FIG. 12 is a model figure showing how the stent bending analysis was conducted.

Figure 13:
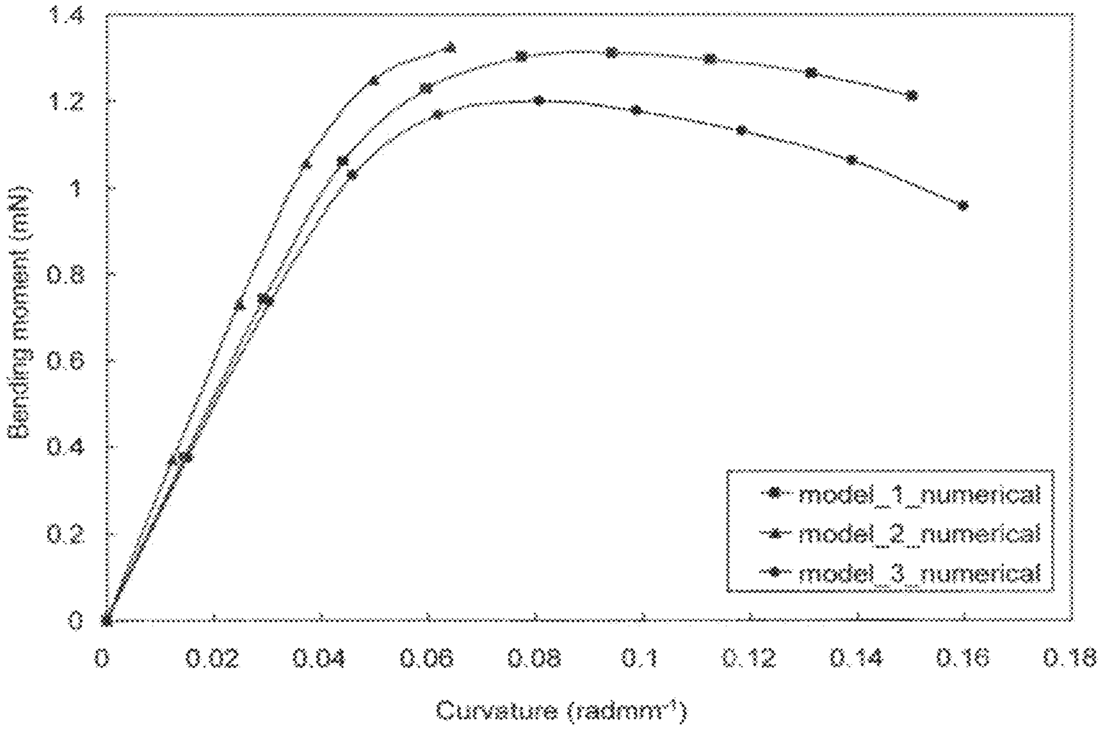

FIG. 13 shows the results of stent bending analysis for pattern A.

Figure 14:
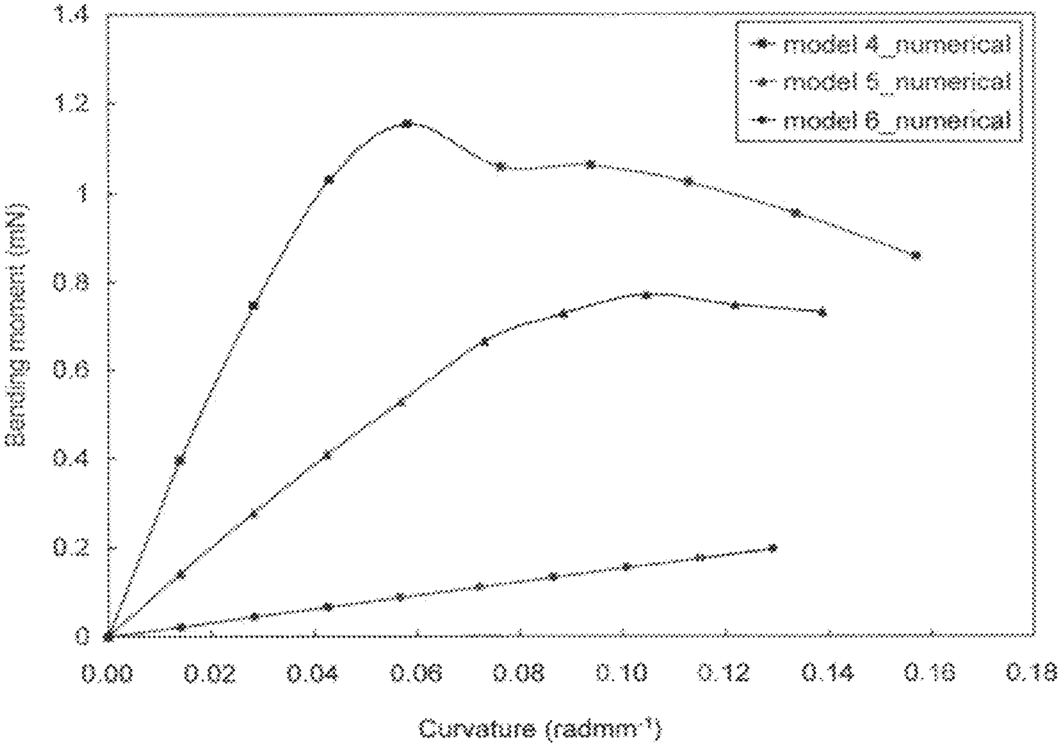

FIG. 14 shows the results of stent bending analysis for pattern B.

Figure 15:
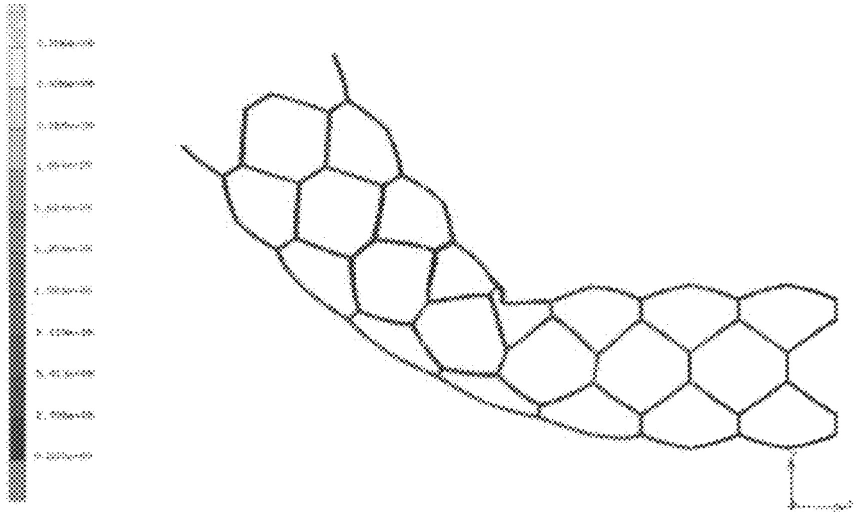

FIG. 15 shows a stent of pattern A that underwent buckling at a curvature of around 0.06 $radmm^{-1}$ in a bending test.

Figure 16:
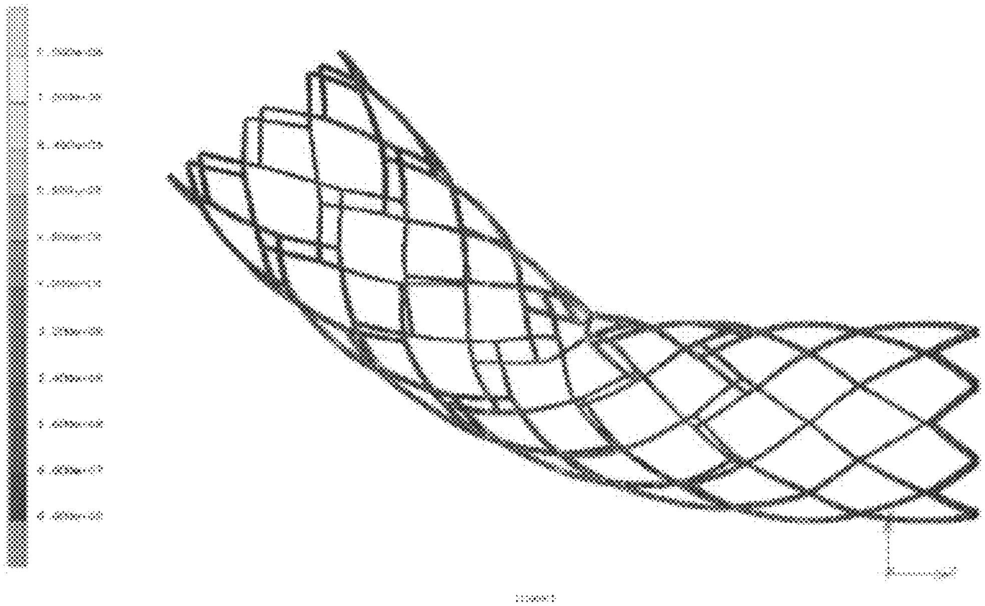

FIG. 16 shows stent model 4 of pattern B that underwent buckling at a curvature of around 0.06 $radmm^{-1}$ in a bending test.

Figure 17:
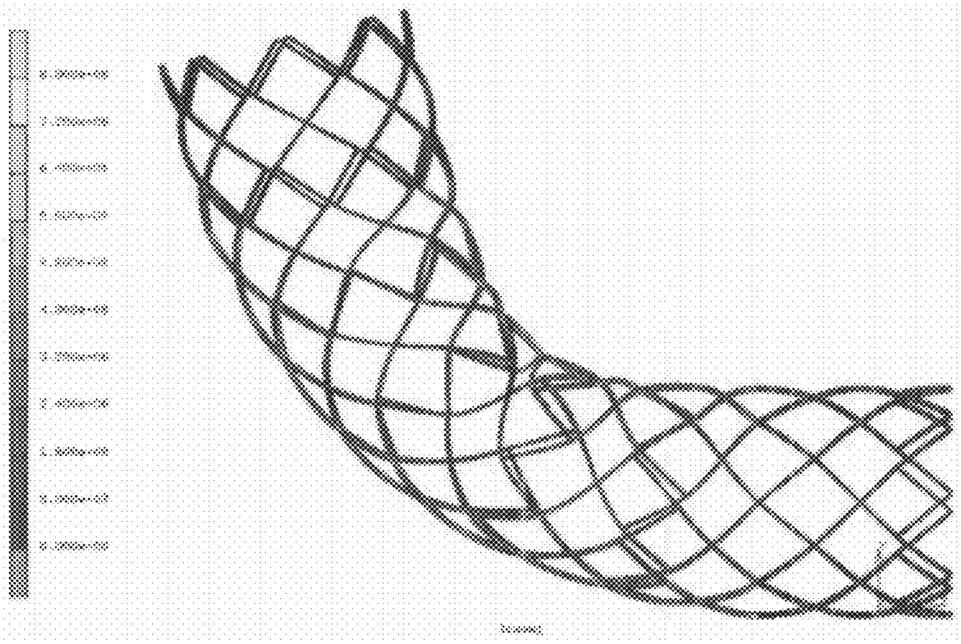

FIG. 17 shows stent model 5 of pattern B that underwent buckling at a curvature of around 0.1 $radmm^{-1}$ in a bending test.

Figure 18:
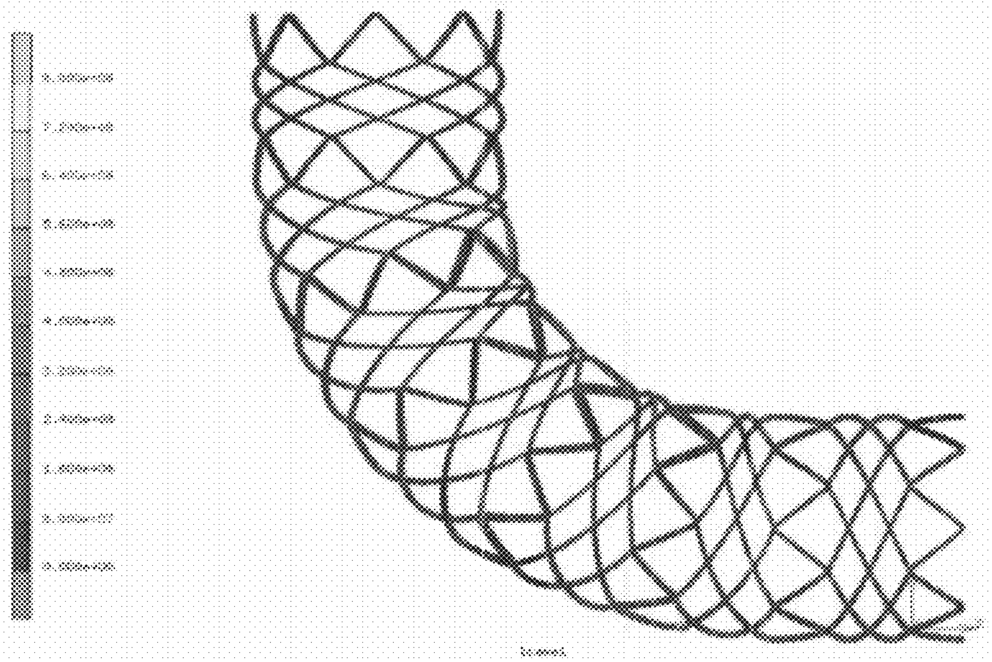

FIG. 18 shows stent model 6 of pattern B at a curvature of around 0.14 $radmm^{-1}$ in a bending test.

Figure 19:
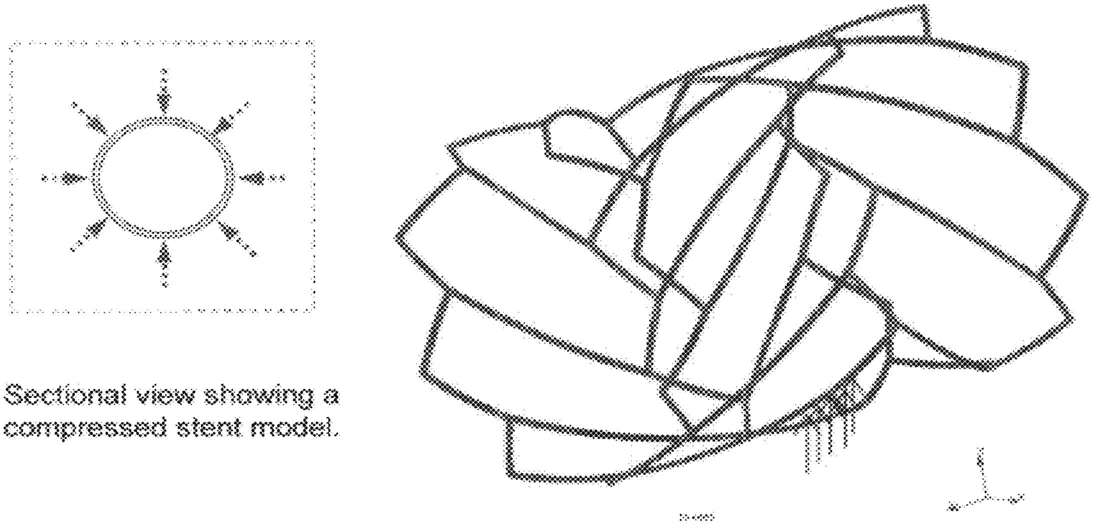

FIG. 19 is a model figure showing how the stent compression analysis was conducted.

Figure 20:
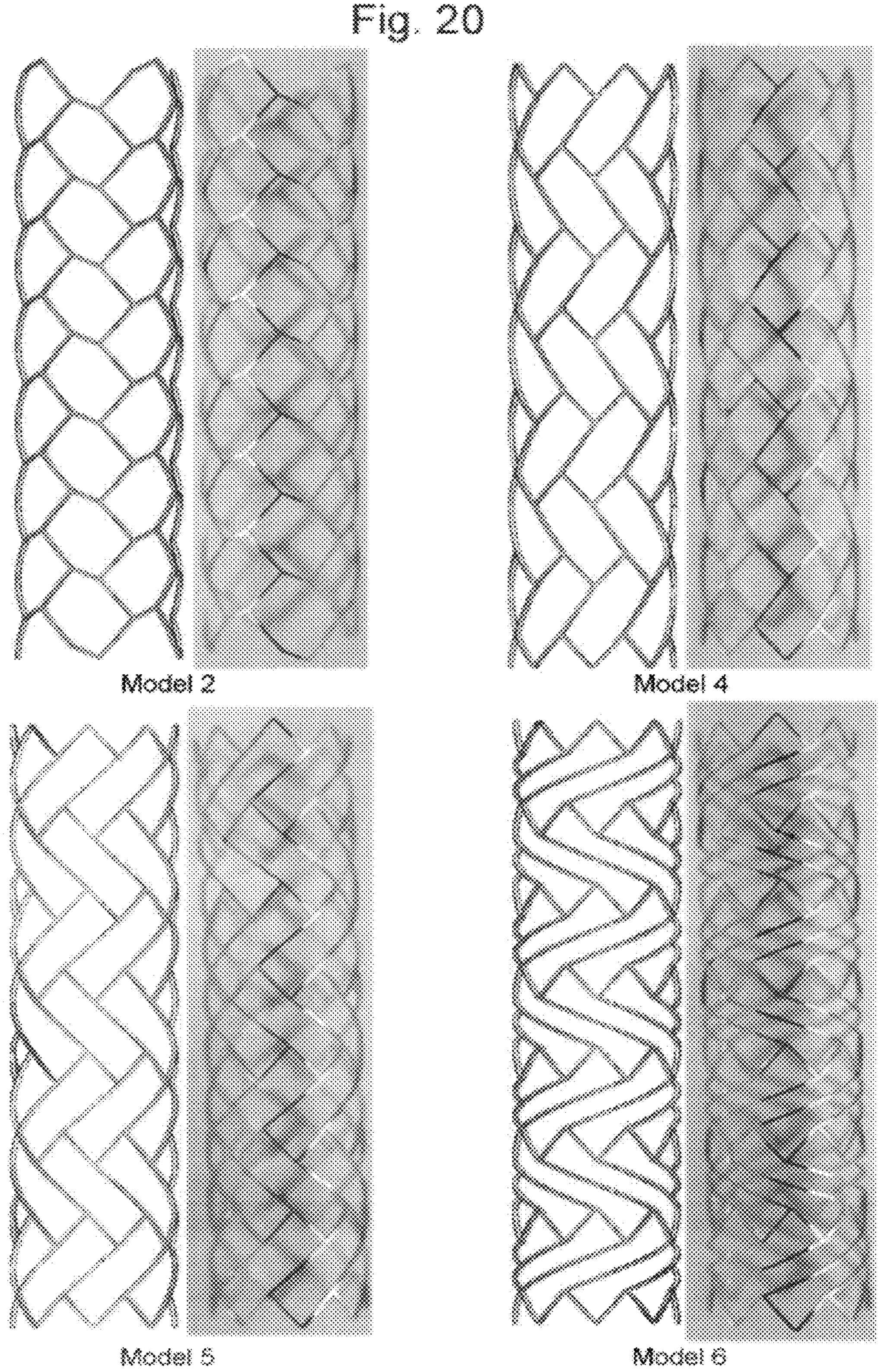

FIG. 20 shows figures and photographs showing actually produced stents.

Figure 21:
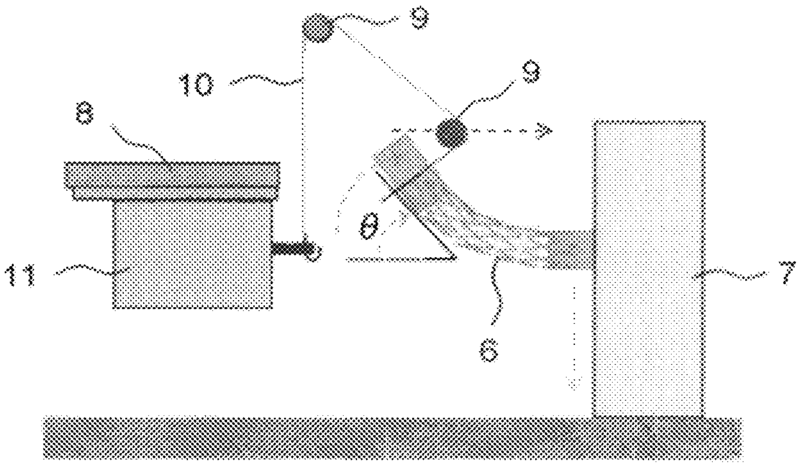
Figure 21:
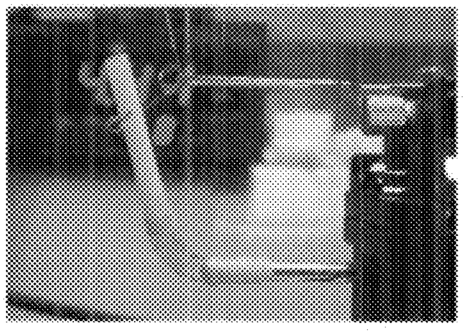

FIG. 21 shows a bending test machine for measuring the longitudinal flexural rigidity of a stent. FIG. 21A shows how the bending test using the bending test machine was conducted. FIG. 21B is a photograph showing the state of the stent during experiment.

Figure 22:
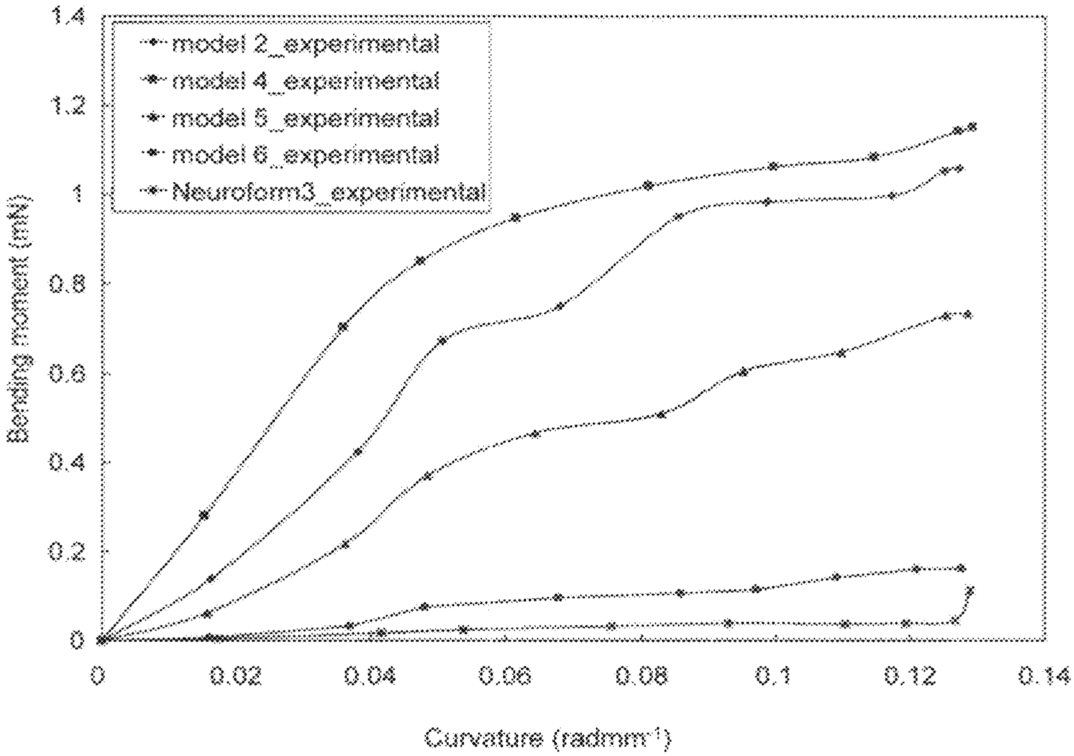

FIG. 22 shows the flexural rigidity (flexibility) of each model.

Figure 23:
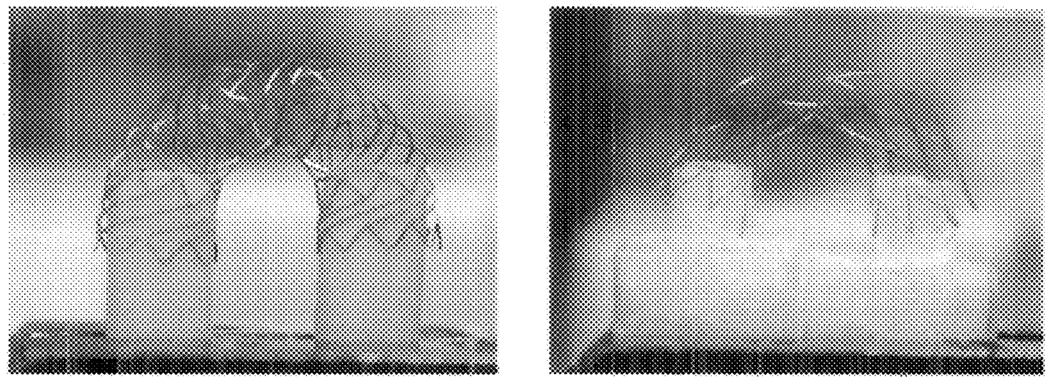

FIG. 23 shows photographs showing the stent (model 6) (FIG. 23A) of the present invention and a stent actually used clinically (FIG. 23B) (Neuroform Stent 3) that were bent and deformed by 180°.

Figure 24:
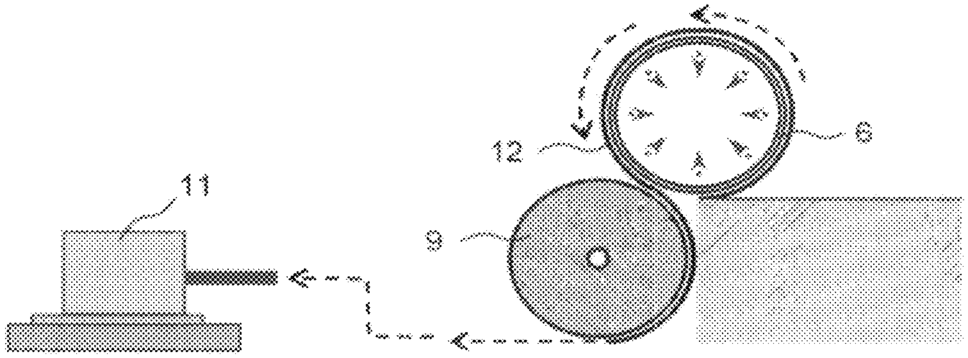
Figure 24:
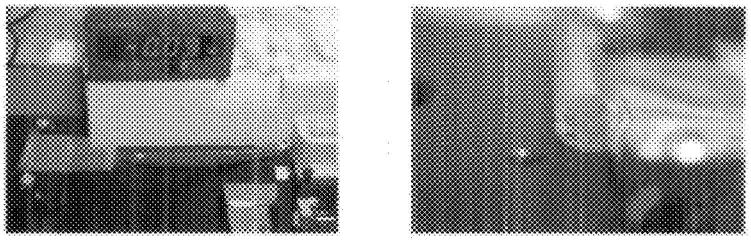

FIG. 24 shows a compression test machine for measuring the radial rigidity of a stent. FIG. 24A shows the whole compression test machine. FIG. 24B is a photograph showing a portion of the test machine.

Figure 25:
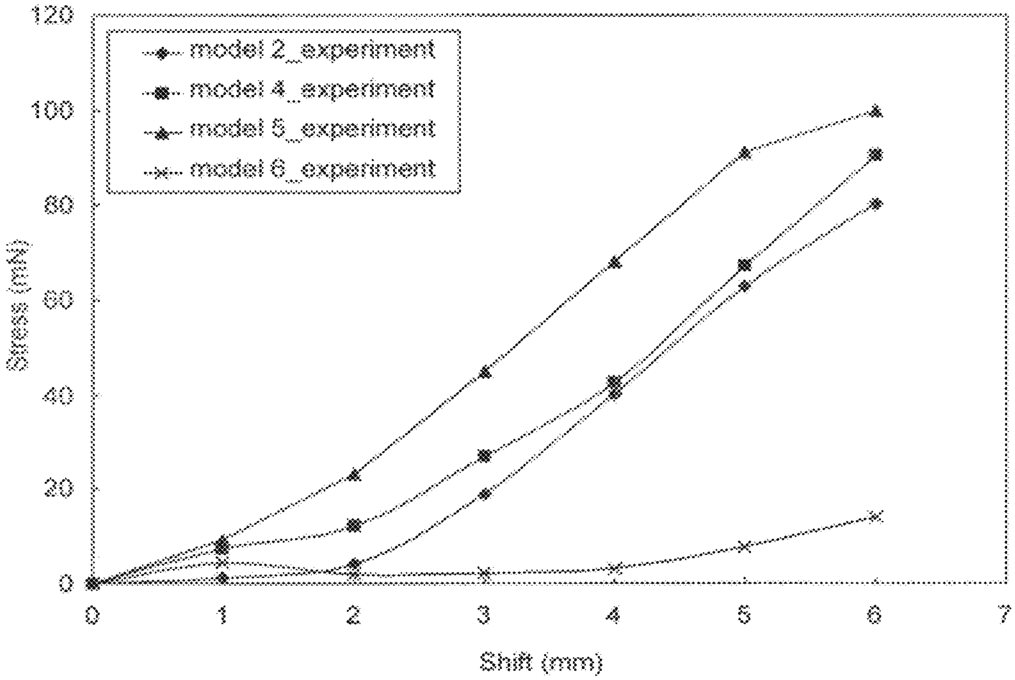

FIG. 25 shows the results of a compression test for measuring the radial rigidity of a stent.

Figure 26:
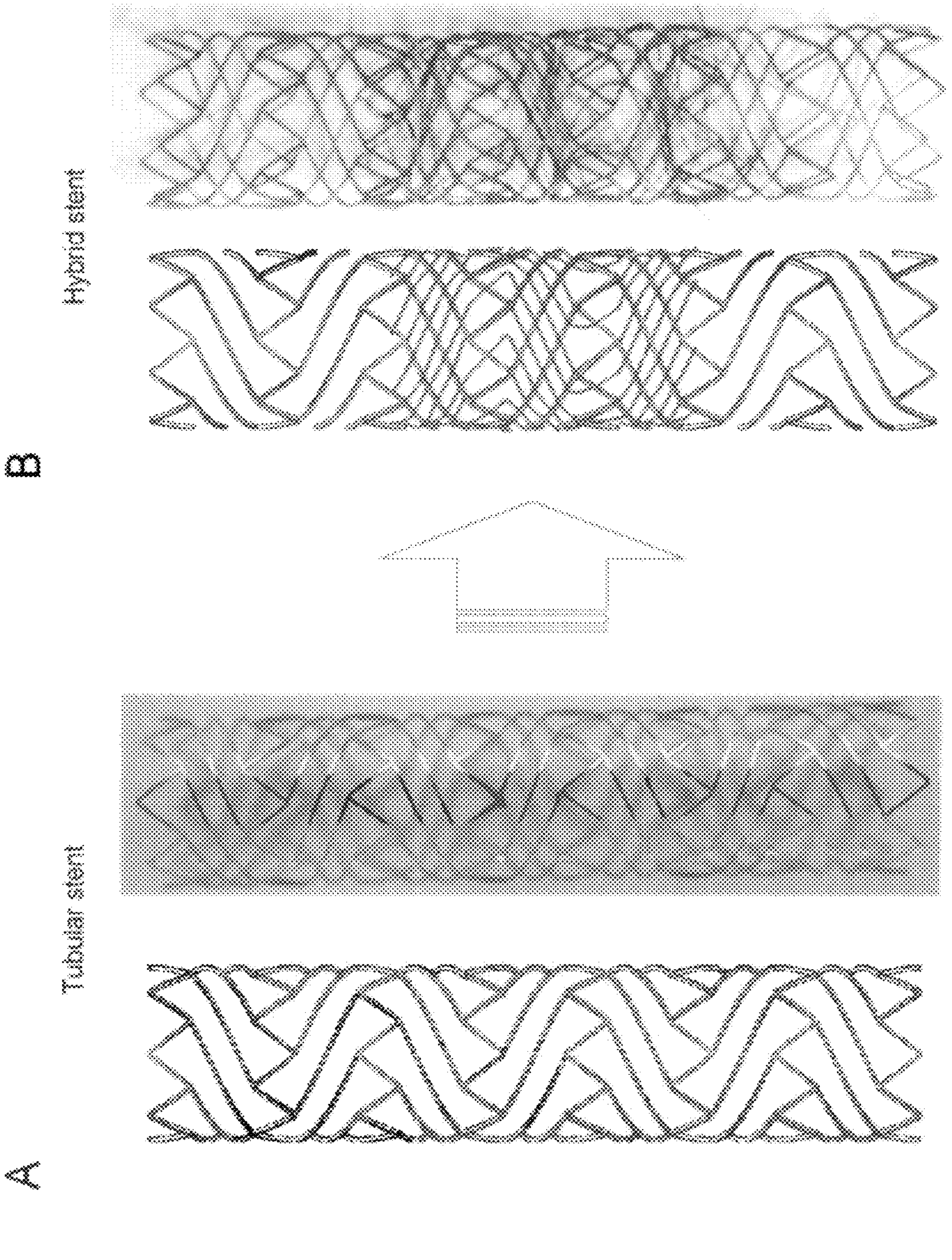

FIG. 26 shows figures and photographs showing the projection drawings of tubular stent (A) and hybrid stent (B).

Figure 27:
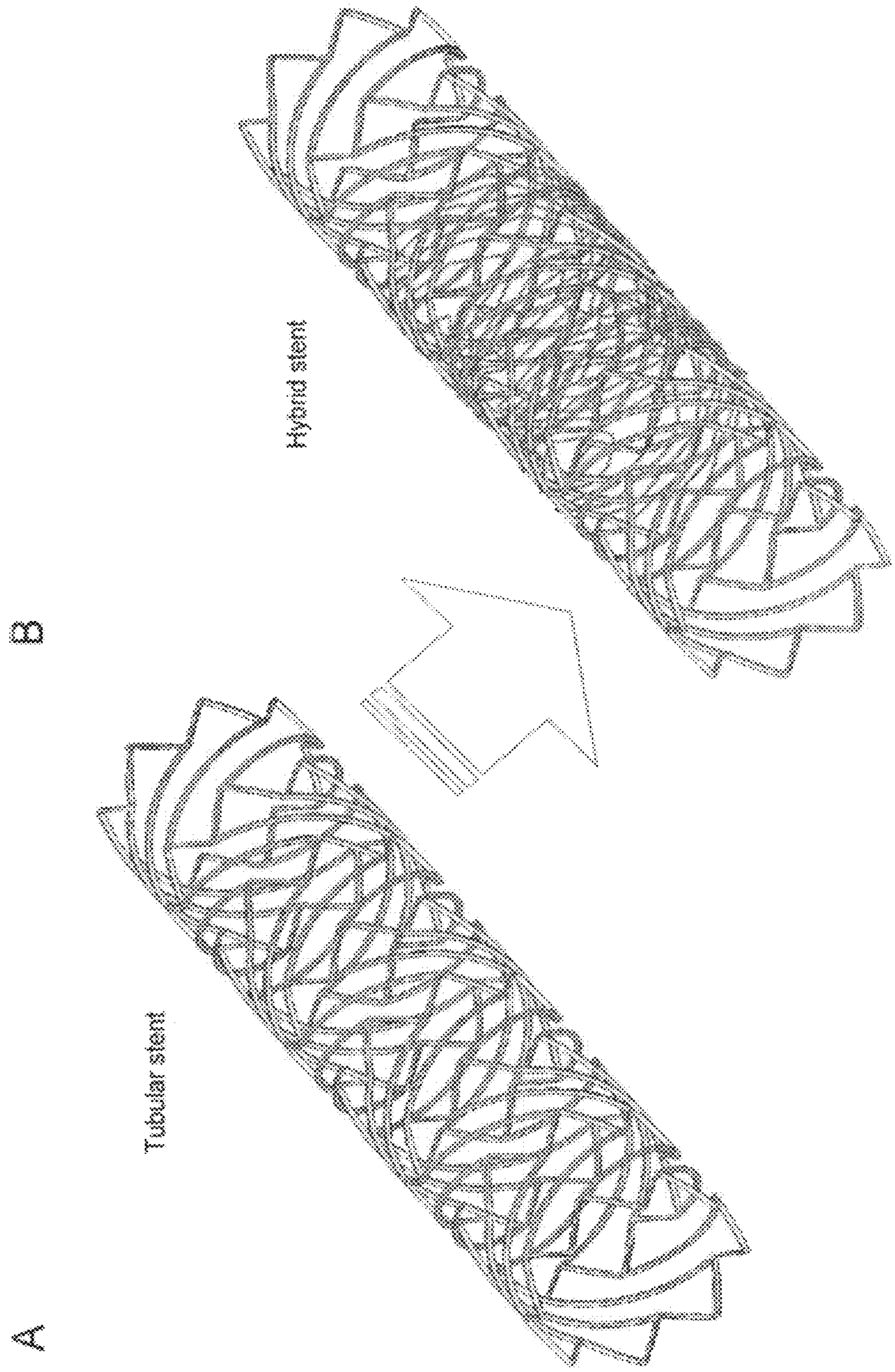

FIG. 27 shows perspective views showing tubular stent (A) and hybrid stent (B).

Figure 28:
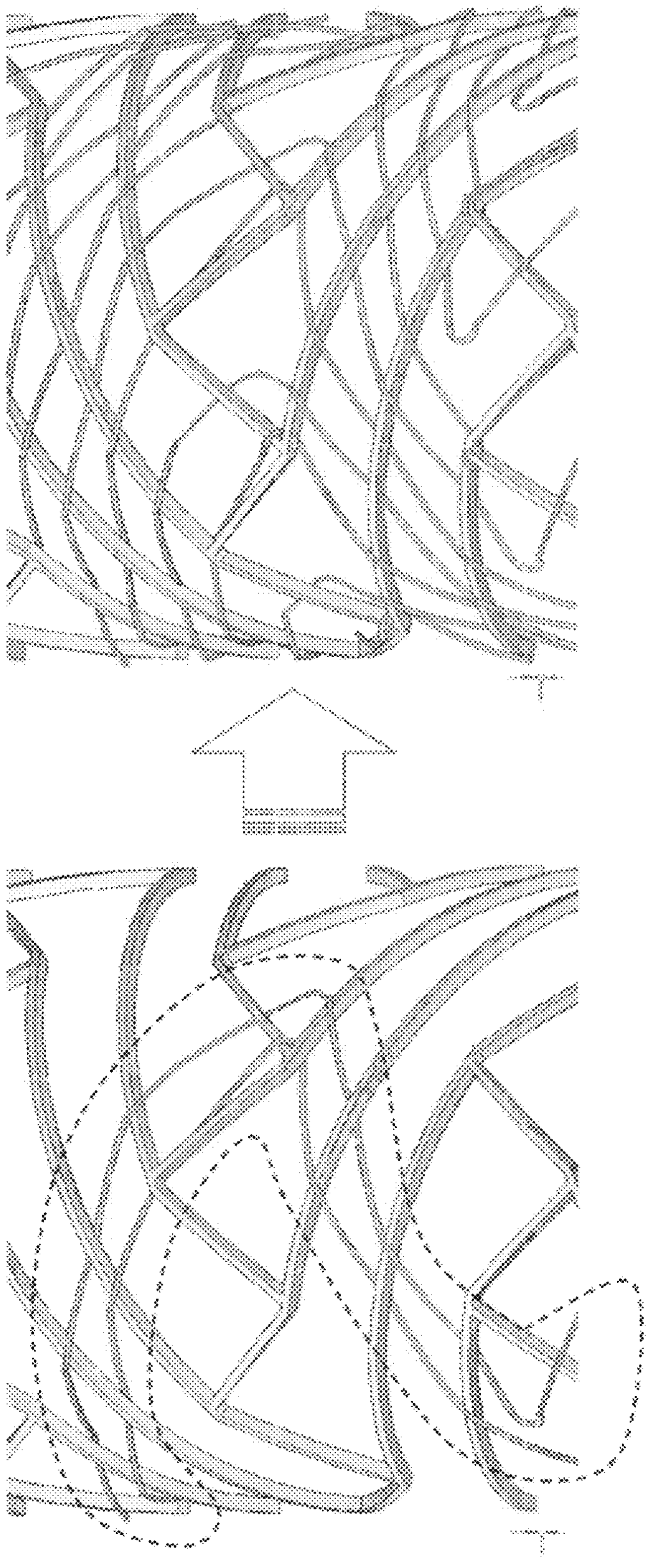

FIG. 28 shows a way of braiding of wires and stent struts in the case of a hybrid stent. FIG. 28A shows a state in which 2 wires are braided and FIG. 28B shows a state in which 8 wires are braided.

Figure 29:
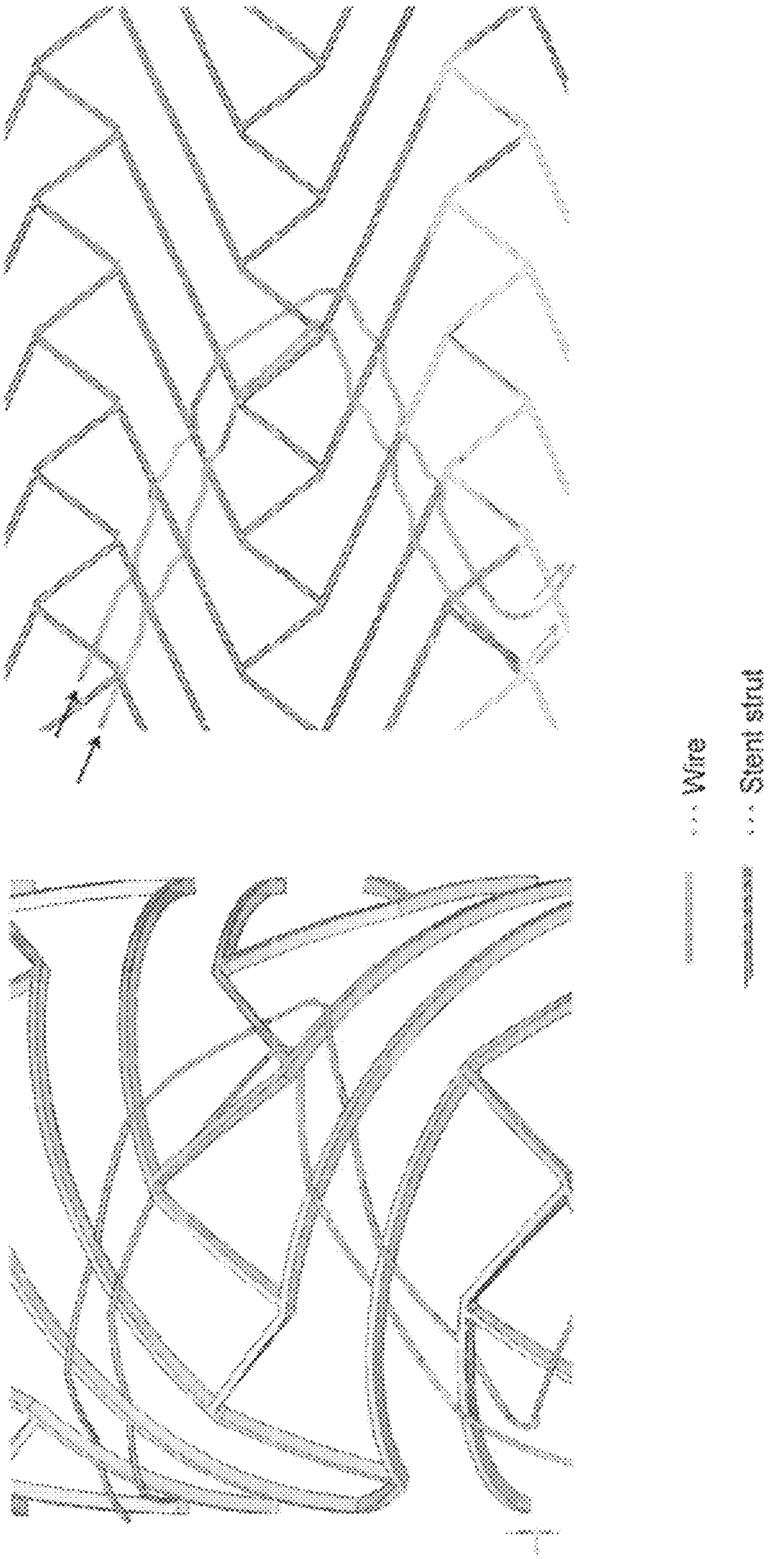

FIG. 29 shows a way of braiding wires and stent struts in the case of a hybrid stent. FIG. 29A sterically shows a state in which 2 wires are braided. FIG. 29B shows a planar state in which 2 wires are braided.

Figure 30:
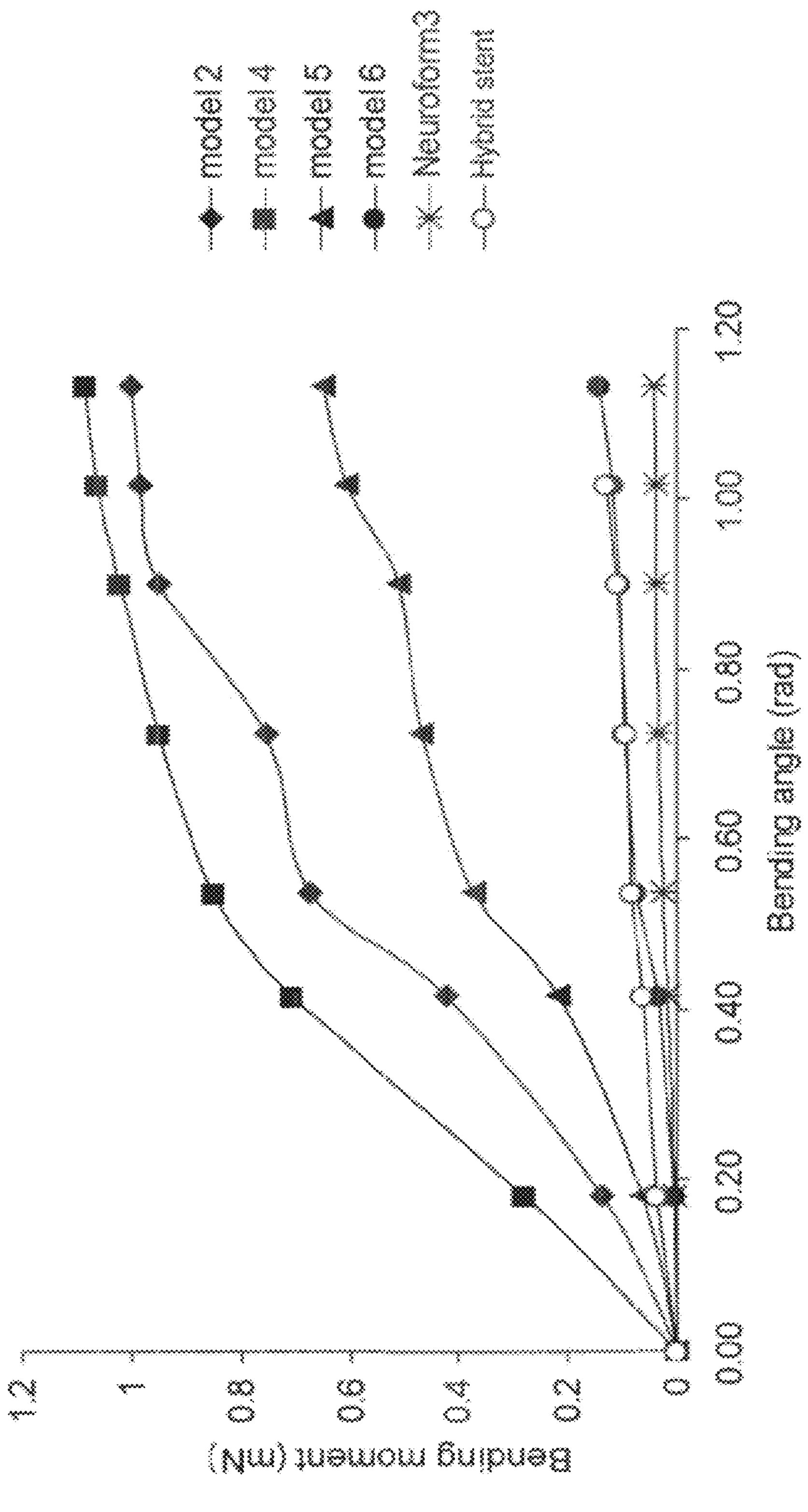

FIG. 30 shows the flexural rigidity (flexibility) of tubular stents and a hybrid stent.

PREFERRED EMBODIMENTS OF THE INVENTION

Hereinafter, the present invention will be described in detail.

Stent Structure

The stent of the present invention has a cylindrical shape.

The wall of the stent has a mesh pattern (network structure) having a plurality of closed cells being adjacent to each other and having certain shapes. A mesh pattern is formed with wire-shaped materials (wire rods) composing the stent. Here, the term "the wall of the stent" refers to a part that separates the inside from the outside of the cylindrical structure of the stent. The term "cell(s)" also refers to opening(s) or compartment(s) that is a part(s) enclosed by wire-shaped materials forming a mesh pattern of the stent. Here, the term "wire-shaped part" forming a mesh pattern of a stent is referred to as a strut. The term "closed cells" refers to cells in which the cells (openings) composing mesh and cells adjacent to the cells share all sides and vertices, cells are not integrated with cells adjacent to the cells, and each cell has a closed structure by the use of wire-shaped materials. On the other hand, when cells (openings) composing mesh and cells adjacent to the cells do not share some sides or vertices and cells are integrated with cells adjacent to the cells, the relevant cells are referred to as open cells. Also, a single cell is referred to as a single closed cell unit.

All (a plurality of) closed cells of the stent of the present invention have congruent shapes and the stent has a planar structure filled with congruent cells on the entire wall of the stent. Specifically, when the cylindrical stent is longitudinally cut open along the contour of cells so as to be developed into a plane (FIG. 1A), the stent has a planar structure filled with cells having congruent shapes according to the Pythagorean tessellation theory. In other words, the whole flatly developed stent has a tessellation (a planform in which cells are filled). It can also be said that the curved surface of the wall of a cylindrical stent is filled with cells having congruent shapes. However, in the present invention, when the wall of cylindrical stent forms a curved surface, the wall is planarly filled with cells having congruent shapes. Here, the term "congruent" refers to "congruent" based on euclidean geometry. A figure created via line-symmetric displacement is also a figure congruent with the other figure.

Figure 1:
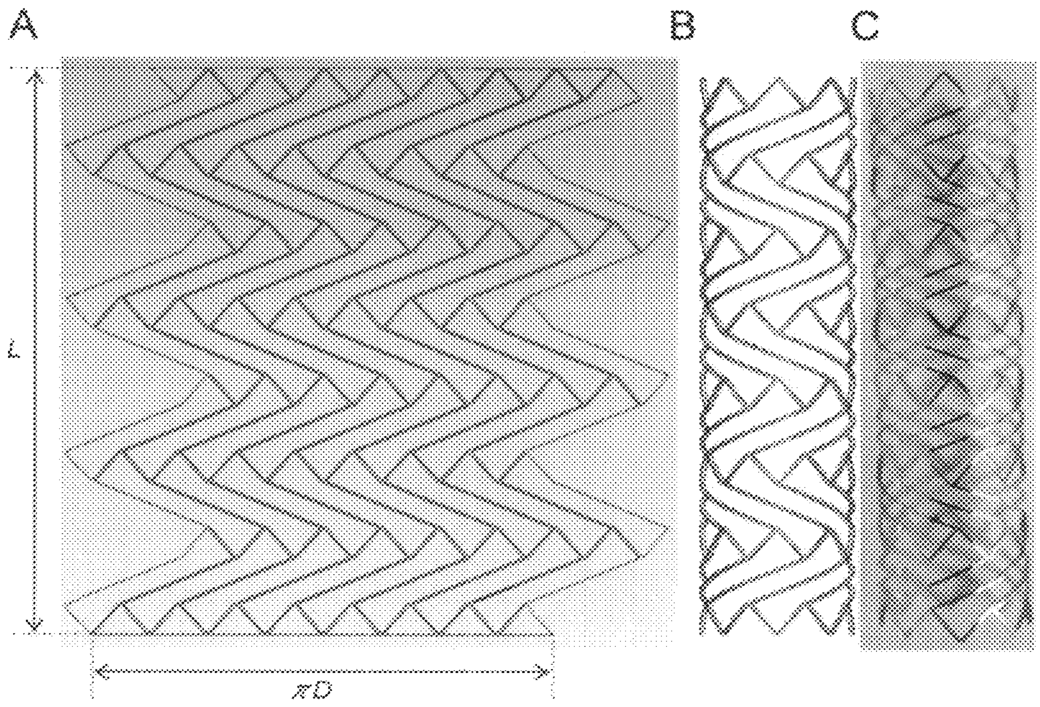
FIG. 1 shows the structure of the stent of the present invention.

FIG. 1A shows a tessellation of the stent of the present invention. The structural interrelationship among closed cells can be understood from FIG. 1A. Also, FIG. 1B shows a projection drawing of a cylindrical stent. Also, FIG. 1C is a photograph showing an actually prepared cylindrical stent. FIG. 1A, FIG. 1B, or FIG. 1C shows an example of the structure of the stent of the present invention. However, the examples of the structures of the stent of the present invention are not limited thereto. The number of closed cells in the longitudinal direction and the number of the same in the circumferential direction of one stent can be appropriately varied depending on the types or the like of in vivo lumen into which the stent is inserted to be placed. Also, the shape of closed cells can be deformed as long as it satisfies the following conditions. When the plane (shown in the form of tessellation) in FIG. 1A is rolled cylindrically so that the contour on the right end and the same on the left end are joined, the cylindrical stent of the present invention shown in FIG. 1B and FIG. 1C can be formed. "L" in FIG. 1A denotes the longitudinal length of the stent. In FIG. 1A, "D" denotes the outer diameter of the cylindrical stent and "πD" denotes the length of the outer perimeter of the stent in the circumferential direction. Also, FIG. 2 is an enlarged view showing the shape of a single closed cell unit.

Mesh patterns of the wall of the stent can be roughly divided into two mesh patterns based on the orientation of the pattern. One mesh pattern is characterized in that all closed cells circumferentially adjacent to each other are congruent and similar in shape (in the present invention, this pattern is referred to as pattern B). The other mesh pattern is characterized in that all closed cells longitudinally adjacent to each other are congruent and similar in shape, but the mesh pattern does not meet the conditions requiring the shapes of closed cells circumferentially adjacent to each other to all be congruent and similar in shape (in the present invention, this pattern is referred to as pattern A).

Figure 2A:
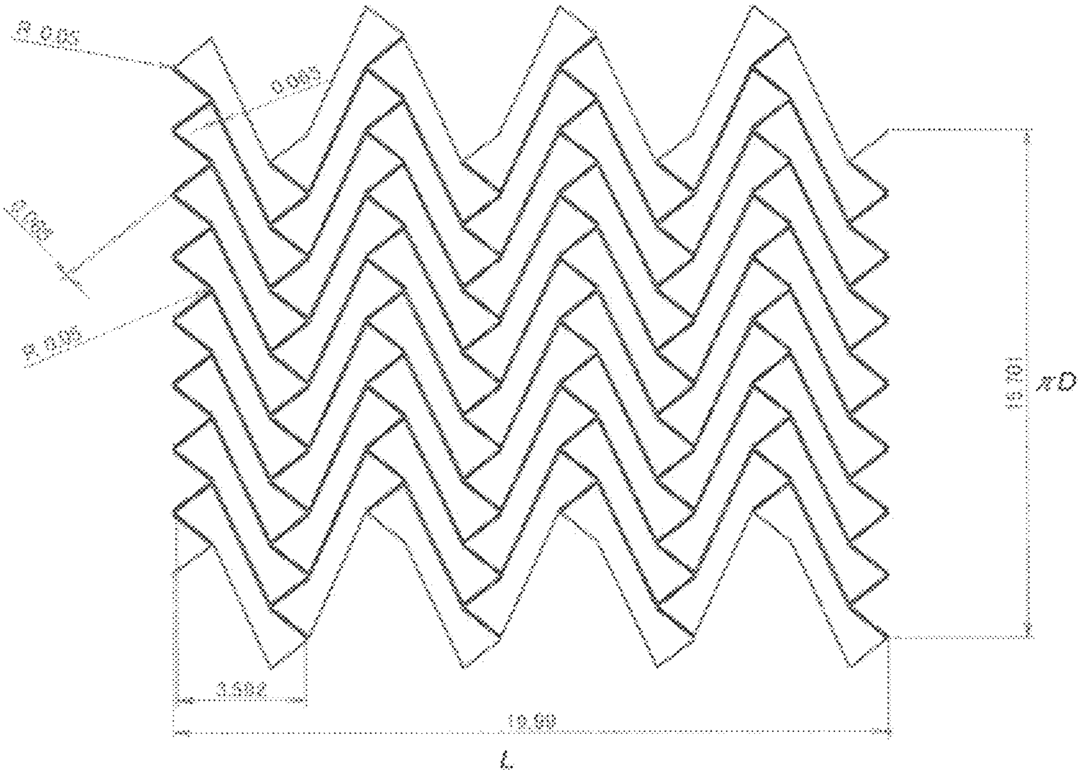
FIG. 2A shows a mesh pattern of the stent wherein all closed cells circumferentially adjacent to each other are congruent and similar in shape.
Figure 2B:
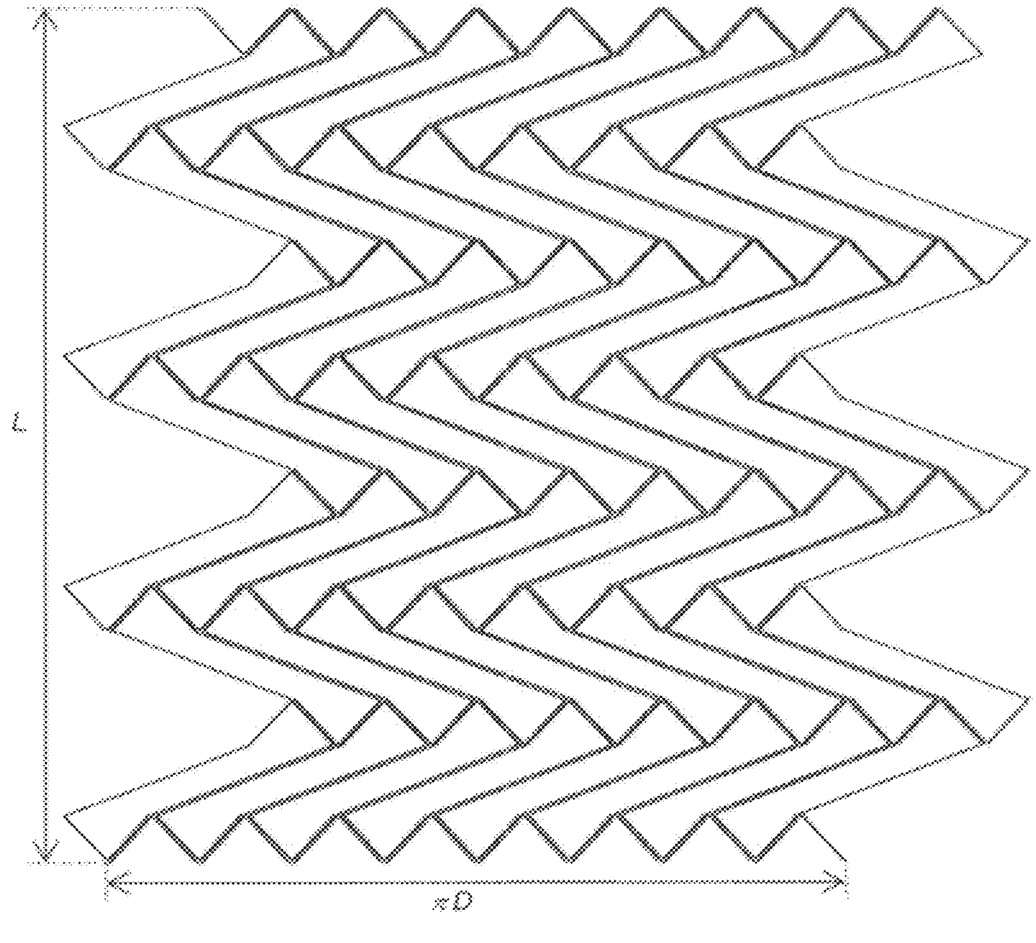
FIG. 2B shows a mesh pattern of the stent wherein all closed cells longitudinally adjacent to each other are congruent and similar in shape, but the mesh pattern does not meet the conditions requiring the shapes of closed cells circumferentially adjacent to each other to all be congruent and similar in shape.

In the present invention, both pattern A and pattern B are encompassed, and pattern B is preferable. Here, the term "closed cells circumferentially adjacent to each other" refers to a plurality of closed cells that are aligned in a line parallel to the circumferential direction when midpoints of sides shared by closed cells adjacent to each other are connected. For example, FIG. 2A shows a mesh pattern wherein all closed cells circumferentially adjacent to each other are congruent and similar in shape. FIG. 2B shows a mesh pattern wherein all closed cells longitudinally adjacent to each other are congruent and similar in shape, but the mesh pattern does not meet the conditions requiring the shapes of closed cells circumferentially adjacent to each other to all be congruent and similar in shape. The pattern of closed cells in FIG. 2A and the pattern of closed cells in FIG. 2B are in a relationship such that the pattern of FIG. 2A is obtained via rotation of the pattern of FIG. 2B by 90° or the pattern of FIG. 2B is obtained via rotation of the pattern of FIG. 2A by 90°. Also, the patterns of FIG. 2A and FIG. 2B can be expressed as follows.

Specifically, a single closed cell unit is adjacent to and shares sides with the other 6 closed cell units. When the two adjacent closed cells are combined, 2 shapes can be formed by the resulting contour. One shape is formed when the two congruent closed cells become one so that the diagonal lines of the two closed cells are parallel to each other. The other shape is formed when closed cells (that are congruent to each other) are combined while sharing different sides and this is L-shaped, V-shaped, or arrow tip-shaped. In the case of a stent having a mesh pattern (FIG. 2A) wherein all closed cells circumferentially adjacent to each other are congruent and similar in shape, a substantially L-shaped, substantially V-shaped, or arrow tip-shaped folded part (vertex) (formed when the two closed cells become one) points to the circumferential direction.

In the case of a stent having a mesh pattern (FIG. 2B) wherein all closed cells longitudinally adjacent to each other are congruent and similar in shape, and in which such mesh pattern does not meet the conditions requiring the shapes of closed cells circumferentially adjacent to each other to all be congruent and similar in shape, a substantially L-shaped, substantially V-shaped, or arrow tip-shaped folded part (vertex) (formed when the two closed cells are united) points to the longitudinal direction.

Furthermore, in the case of a stent having a mesh pattern (FIG. 2A) wherein all closed cells circumferentially adjacent to each other are congruent and similar in shape, an x-y coordinate grid (FIG. 4) is superimposed on a flatly developed plan view (FIG. 1A) (created by cutting open the stent longitudinally along the contour line of closed cells), so that the circumferential direction corresponds to the x axis, the longitudinal direction corresponds to the y axis, and vertex p3 (FIG. 3) located between side p2p3 (side 2) and side p3p4 (side 3) of closed cells existing on an end of the stent is present on the x axis. On the other hand, in the case of a stent having the mesh pattern (FIG. 2B) wherein all closed cells longitudinally adjacent to each other are congruent and similar in shape, but the mesh pattern does not meet the conditions requiring all closed cells circumferentially adjacent to each other to be congruent and similar in shape, when an x-y coordinate grid (FIG. 4) is superimposed on a flatly developed plan view (FIG. 1A) (created by cutting open the stent longitudinally along the contour line of closed cells), so that the circumferential direction corresponds to the x axis, the longitudinal direction corresponds to the y axis of the xy coordinate grid, and vertex p3 (FIG. 3) located between side p2p3 (side 2) and side p3p4 (side 3) of closed cells existing on an end of the stent is present on the y axis.

The mesh pattern in FIG. 2A is pattern B and the mesh pattern in FIG. 2B is pattern A.

Figure 3:
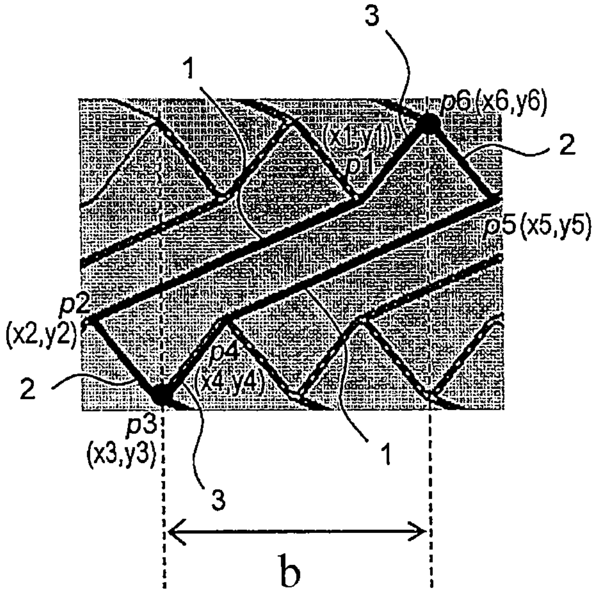
FIG. 3 shows the shape of a closed cell forming a mesh pattern of the stent of the present invention.
Figure 4:
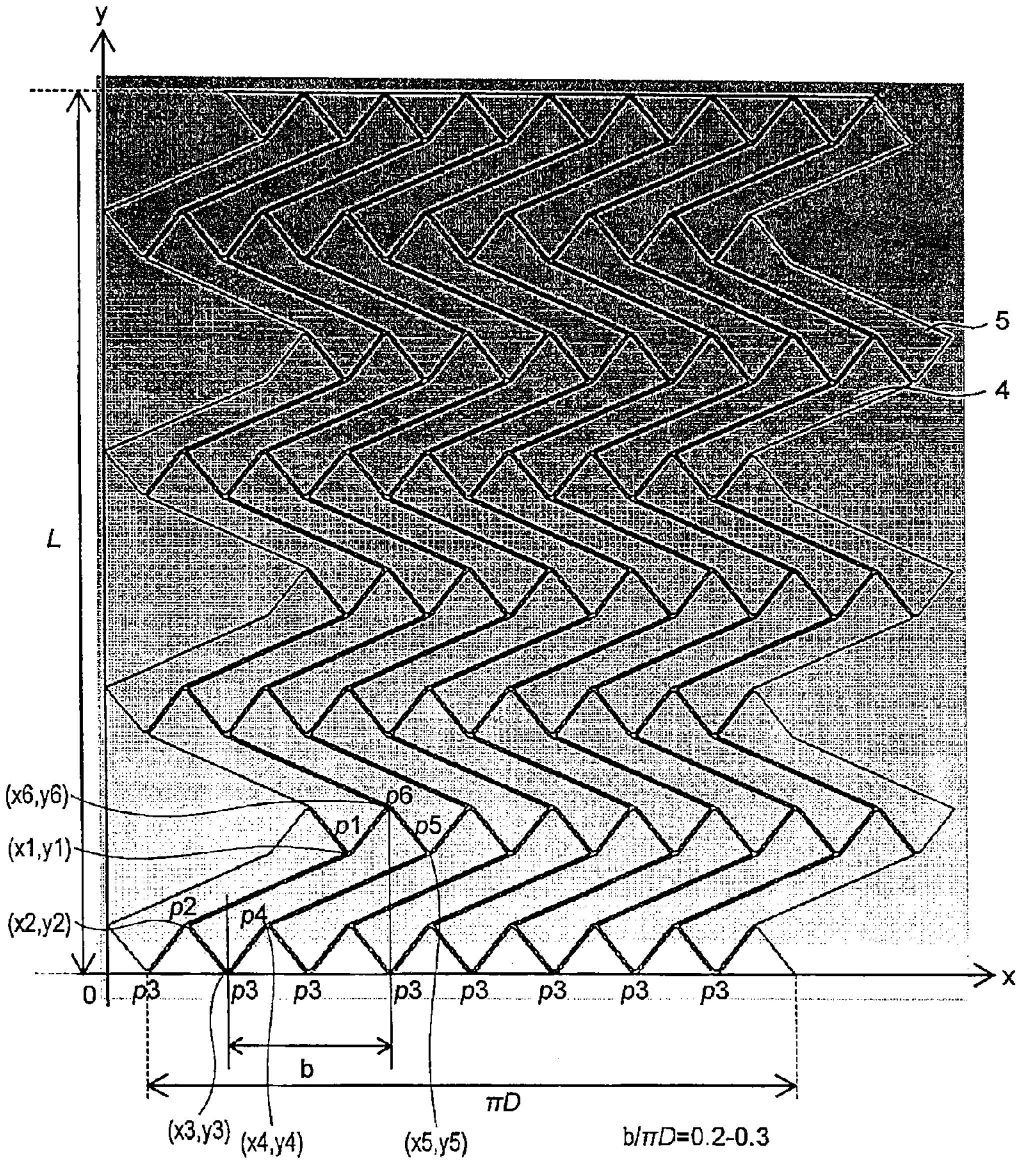
FIG. 4 is a plan view of the stent of the present invention superimposed on an xy coordinate grid.

A single closed cell unit composing the wall of a stent has a hexagonal shape. On the basis of the Pythagorean tessellation theory, congruent parallel hexagons (in which 3 pairs of opposite sides are parallel and equal) can form a tessellation. Closed cells composing the wall of the stent of the present invention preferably have parallel hexagonal shapes that can at least form a tessellation. Closed cells composing the wall of the stent of the present invention preferably has the following graphic (figural) characteristics as shown in FIG. 3. In addition, the following graphic characteristics are those when a cylindrical stent is developed on a plane, closed cells having the following graphic characteristics fill the curved surface of the cylindrical stent. Accordingly, when such a cylindrical stent is shown in the projection drawing in FIG. 1B, the shapes of closed cells can be deformed. In particular, when the sizes of single closed cell units are the same, the lower the outer diameter of the stent, the higher the degree of deformation of the same on such a projection drawing. However, in the present invention, as long as closed cells (when developed on a plane) have the following characteristics, even if the shapes of closed cells on the projection drawing of the stent are deformed, the closed cells of the cylindrical stent have the graphic characteristics of the closed cells of the present invention.

(i) Closed cells have substantially concave hexagonal shapes. The term "concave hexagon" refers to a hexagon wherein one or more of the 6 interior angles are greater than 180°.

(ii) The interior angles at 2 out of 6 vertices are each greater than 180° and other 2 vertices are located between the 2 vertices. Specifically, the 2 vertices having interior angles of 180° or more are a pair of corresponding vertices in the hexagon. Also, the above 2 out of 6 vertices have the interior angles of greater than 180° (as described above) and preferably less than 270°.

(iii) A closed cell has a substantially parallel hexagonal shape comprising a pair of substantially parallel sides 1 having substantially the same lengths, a pair of substantially parallel sides 2 having substantially the same lengths, and a pair of substantially parallel sides 3 having substantially the same lengths, wherein the interior angles at vertices (2 vertices are present) that are end points (shared by sides 1 and sides 3) located between the above sides 1 and sides 3 are each greater than 180°. Here, the lengths of segments of sides 1, 2, and 3 are not limited. Examples thereof include a case in which sides 1 are longer than sides 3 and a case in which sides 1 are longer than sides 2 and sides 3.

(iv) A closed cell is a point-symmetric hexagon. Here, the term "point-symmetric (hexagon)" refers to a hexagon that is identical to the original hexagon when it is rotated by 180° about the center of the hexagon.

(v) A closed cell is divided by any straight line that passes through the symmetrical center point into 2 congruent graphics or graphic groups.

In the present invention, examples of the substantially concave hexagon include a concave hexagon, examples of the substantially parallel hexagon include a parallel hexagon, and examples of the term "substantially parallel" include "parallel," and examples of the term "substantially the same" include "the same."

Regarding the number of closed cells composing the wall of a stent, "M" closed cells (M units) are longitudinally present adjacent to each other and "N" closed cells (N units) are circumferentially present adjacent to each other. When they are shown in FIG. 1A, M=7 and N=8.

"M" closed cells ("M" denotes the number of closed cells) ranges from 4 to 20 and "N" closed cells ("N" denotes the number of closed cells) ranges from 4 to 36 and preferably ranges from 4 to 16. The longitudinal length (L) ranges from 5 mm to 100 mm, preferably ranges from 10 mm to 50 mm, and further preferably ranges from 15 mm to 30 mm. Also the outer diameter (D) of a stent ranges from 1.5 mm to 50 mm, preferably ranges from 1.5 mm to 10 mm, and further preferably ranges from 1.5 mm to 5 mm. Also, the wall thickness (t) of a stent ranges from 45 μm to 300 μm and preferably ranges from 45 μm to 150 Furthermore, the width (w) of wires (struts) forming a mesh pattern of the outer wall of a stent ranges from 40 μm to 300 μm and preferably ranges from 40 μm to 150 μm.

The mesh pattern of a stent represented by model 5 or a stent represented by model 6 in FIG. 8B is pattern B and the shapes of closed cells are concave hexagonal shapes.

The values of these L, D, t, and w determine the size of the stent. These values can be appropriately determined depending on the applications of the stent. Also, the values of M and N determine the size of closed cells of the wall of the stent and the density of closed cells of the entire stent. These values can be appropriately determined depending on the applications of the stent, flexibility required for the stent, and the like.

Note that "h=L/M" denotes "cell length" and "1=πD/N" denotes cell width. These values are naturally determined after the above M, N, L, and D are determined.

Also, closed cells composing the wall of the stent of the present invention have the following characteristics.

Figure 5:
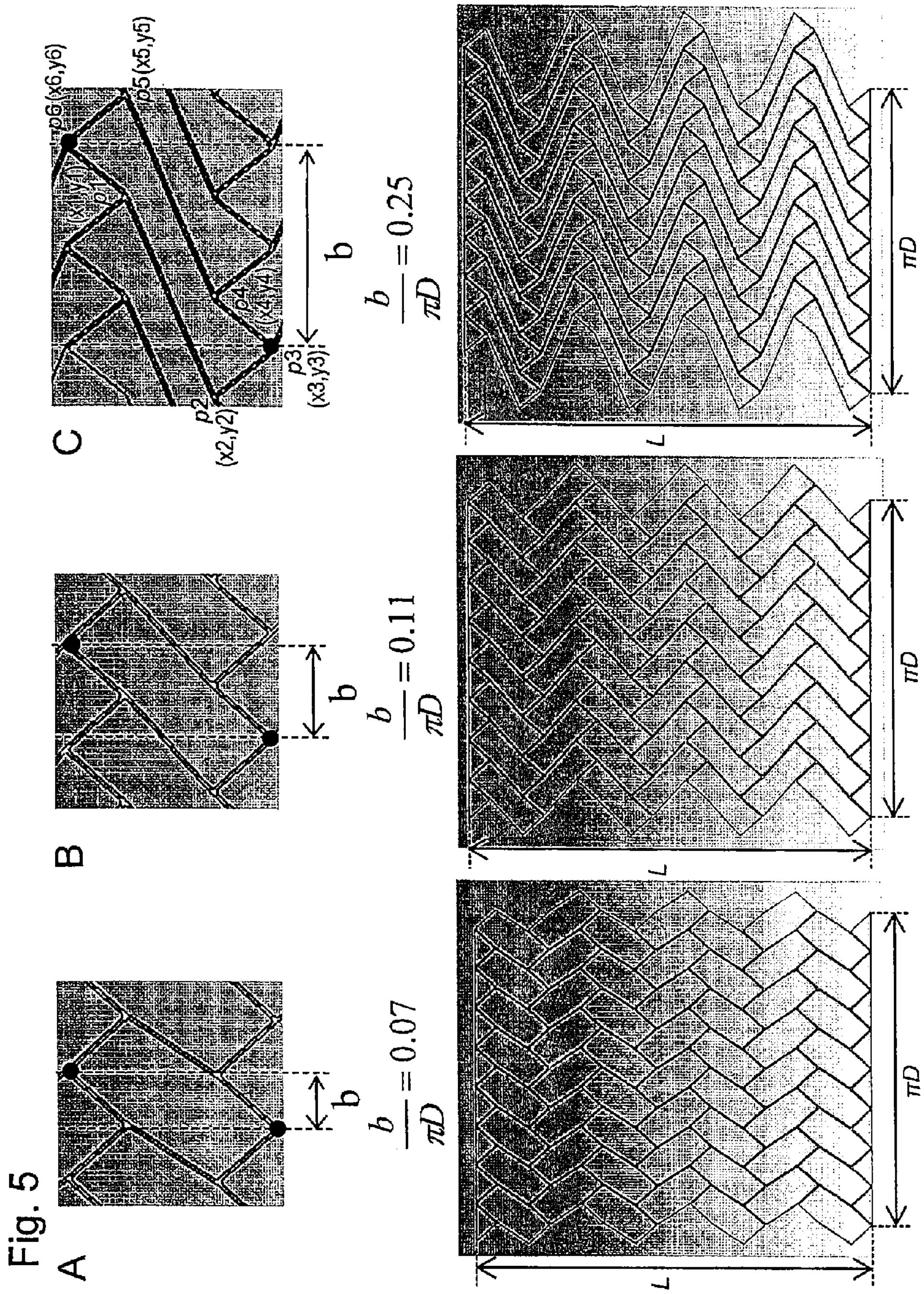
FIG. 5 shows a flatly developed plan view of the stent, a single closed cell unit, and the value of b/πD when.

When the outer diameter of the stent is determined to be "D" and the distance between vertex p6 and p3 that are each located between side 2 and side 3 (two sides of a single closed cell unit) in the circumferential of the stent is denoted by "b" as shown in FIG. 3, b/πD (πD indicates the outer circumferential length of the stent) ranges from 0.03 to 0.5, preferably ranges from 0.10 to 0.5 or 0.11 to 0.5, further preferably ranges from 0.15 to 0.4, further more preferably ranges from 0.2 to 0.3, and even further more preferably ranges from 0.23 to 0.27, and is particularly preferably 0.25. In the present invention, "b" may also be referred to as "gap (or shift)" of vertices of cells in the circumferential direction of the stent. When b/πD is within the above range, the thus obtained stent is rich in flexibility. In addition, FIG. 5 shows a flatly developed plan view of the stent, a single closed cell unit, and the value of b/πD when:

- closed cells are convex hexagons (in which all interior angles are each less than 180°) (FIG. 5A);
- closed cells are concave hexagons with interior angles of greater than 180°, wherein the interior angles are each slightly greater than 180° (FIG. 5B); or
- closed cells are concave hexagons with interior angles of greater than 180°, wherein the interior angles are each far greater than 180° (FIG. 5C).

As described later, a stent having the structure of FIG. 5A lacks flexibility, a stent having the structure of FIG. 5B has good flexibility, and a stent having the structure of FIG. 5C has even better flexibility. Examples of the stent of the present invention include preferably a stent shown in FIGS. 5B and C, having closed cells with concave hexagonal shapes and good flexibility, and specifically, a stent wherein the above b/πD of a single closed cell unit is 0.1 or more. For example, in the case of M=7 closed cells, N=8 closed cells, L=20 mm, D=5 mm, and b/πD of 0.1 or more, closed cells have concave hexagonal shapes.

Also, when closed cells composing the wall of the stent of the present invention are represented by substantially concave hexagon P: p1, p2, p3, p4, p5, and p6 (FIG. 3), side p1p2 (side 1) and side p4p5 (side 1) are substantially the same in length and substantially parallel to each other, side p2p3 (side 2) and side p5p6 (side 2) are substantially the same in length and substantially parallel to each other, side p3p4 (side 3) and side p6p1 (side 3) are substantially the same in length and substantially parallel to each other, and the interior angles at vertex p1 and vertex p4 are each greater than 180°. Also, when a flatly developed plan view (FIG. 1A and FIG. 4) created by cutting open the stent longitudinally along the contour line of closed cells is superimposed on an xy coordinate grid, so that vertex p3 (or vertex p6 located between side p5p6 (side 2) and side p6p1 (side 3)) located between side p2p3 (side 2) and side p3p4 (side 3) of a plurality of closed cells circumferentially adjacent to each other is present on the x axis of the xy coordinate grid (FIG. 4), and the coordinates of vertices p1, p2, p3, p4, p5, and p6 of any single closed cell unit are determined to be (x1, y1), (x2, y2), (x3, y3), (x4, y4), (x5, y5), and (x6, y6), respectively, the absolute value for distance x6-x3 between vertex p3 and vertex p6 on the x axis is denoted by "b" in FIG. 3 and b/πD is in the above range.

Figure 2C:
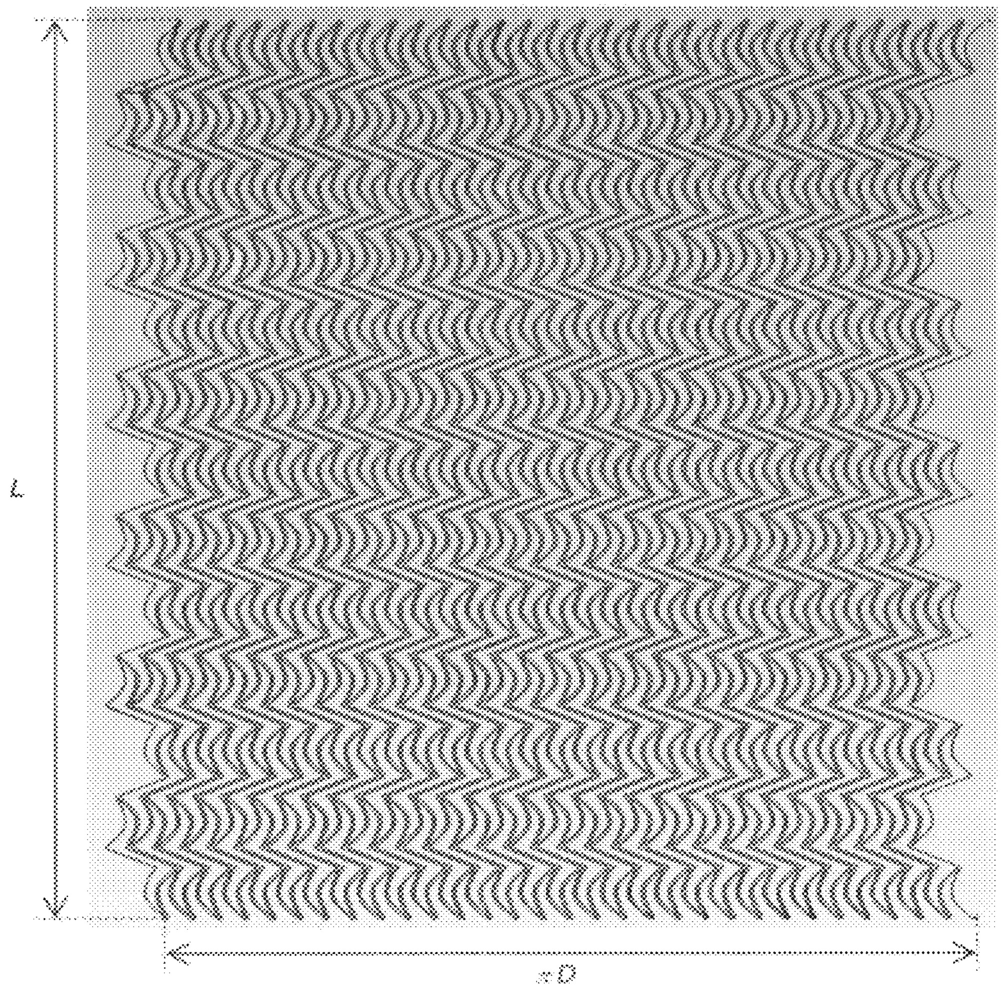

Side 2 and side 3 (side p2p3 (side 2), side p5p6 (side 2), side p3p4 (side 3), and side p6p1 (side 3) in concave hexagon P) of closed cells of the stent of the present invention may be non-linear and curved to form an arc (FIG. 2C). Also in this case, the shapes of closed cells are substantially concave and substantially parallel hexagons, wherein side p2p3 (side 2) and side p5p6 (side 2) are substantially parallel to each other and side p3p4 (side 3) and side p6p1 (side 3) are also substantially parallel to each other. Such closed cells are also included in the closed cells of the present invention.

Except for a case when the shape of a single closed cell unit is line-symmetrical (when side p1p2 (side 1) and side p6p1 (side 3) of concave hexagon P are the same in length), closed cells having 2 types of shape, which are congruent to each other, are present among closed cells composing the wall of the stent. When the shape of a closed cell is inverted, it is identical to the shape of the other closed cell. For example, when closed cells are designated as closed cells I (a closed cell denoted by symbol 4 in FIG. 4) and the other closed cells are designated as closed cells II (a closed cell denoted by symbol 5 in FIG. 4) and the mesh pattern is characterized in that all closed cells circumferentially adjacent to each other are congruent and similar in shape, closed cells I are adjacent to each other and closed cells II are adjacent to each other in the circumferential direction of the stent, but closed cells I and closed cells II do not exist together in the circumferential direction. Also, closed cells I and closed cells II exist alternately in the longitudinal direction of the stent (FIG. 2A). On the other hand, in the case of a mesh pattern wherein all closed cells longitudinally adjacent to each other are congruent and similar in shape, but the mesh pattern does not meet the conditions requiring the shapes of closed cells circumferentially adjacent to each other to all be congruent and similar in shape, closed cells I are adjacent to each other and closed cells II are adjacent to each other in the longitudinal direction of the stent, but closed cells I and closed cells II do not exist together in the longitudinal direction. Also, closed cells I and closed cells II exist alternately in the circumferential direction of the stent (FIG. 2B).

In the case of the stent of the present invention having the mesh pattern wherein all closed cells circumferentially adjacent to each other are congruent and similar in shape, wires (struts) of the wall of the stent will never protrude outside or inside and wires (struts) at the stent ends do not expand in a flared shape, because of its structure.

Furthermore, the present invention encompasses a method for designing a stent to be inserted to be placed and used in the inner cavity of an in vivo tubular organ.

When a stent having the mesh pattern wherein the entire wall of the stent is planarly filled with closed cells having congruent hexagonal shapes is designed by the design method so that "M" (number of cells; M units) closed cells composing the wall of the stent exist adjacent to each other in the longitudinal direction and "N" (number of closed cells; N units) closed cells exist adjacent to each other in the circumferential direction, M, N, longitudinal length (L), the outer diameter (D) of the stent, the wall thickness "t" of the stent, and the width (w) of wires (struts) forming the network structure of the outer wall of the stent are used as parameters and the stent is designed by varying these values for the parameters.

A stent can be designed by varying the parameters on a computer.

Functional Characteristics of Stent

The stent of the present invention has mechanical flexibility. Here, the term "mechanical flexibility" refers to mainly "ease of bending" in the longitudinal direction. For example, mechanical flexibility can be represented using a bending moment when an object is bent until a specific curvature is obtained. Also, the stent of the present invention can be compressed so as to decrease the outer diameter. When the sent is inserted into an in vivo tubular organ, it can be compressed. The compressed stent placed in a tubular organ is self-expandable.

Production of Stent

Preferable materials for the stent of the present invention have their own high rigidity and high biocompatibility. Examples of such materials include titanium, nickel, stainless steel, platinum, gold, silver, copper, iron, chromium, cobalt, aluminium, molybdenum, manganese, tantalum, tungsten, niobium, magnesium, and calcium or alloys including them. Also, synthetic resin materials such as polyolefin such as PE and PP, polyamide, polyvinyl chloride, polyphenylenesulfide, polycarbonate, polyether, and polymethyl methacrylate can be used. Moreover, biodegradable resins (biodegradable polymers) such as polylactic acid (PLA), polyhydroxybutyrate (PHB), polyglycolic acid (PGA), and poly $\epsilon$ caprolactone can also be used. In particular, titanium, nickel, stainless steel, platinum, gold, silver, copper, and magnesium or alloys containing them are desirable. Examples of alloys include an Ni—Ti alloy, a Cu—Mn alloy, a Cu—Cd alloy, a Co—Cr alloy, a Cu—Al—Mn alloy, an Au—Cd—Ag alloy, a Ti—Al—V alloy, and alloys of magnesium with Zr, Y, Ti, Ta, Nd, Nb, Zn, Ca, Al, Li, Mn, or the like. A particularly desirable alloy is an Ni—Ti alloy.

The stent of the present invention can be produced using a tube made of metal, alloy, or resin listed above. Specifically, a metal tube is processed by laser cutting, etching, or the like so as to form the above mesh pattern on the wall of the stent. It is formed particularly preferably by laser cutting. A commercially available laser cutting machine may be used for laser cutting. For example, a stent processor, Microworx Stent (LTT APPLIKATION, Germany) can be used. Such a stent that is prepared by processing a metal tube or the like by laser cutting, etching, or the like is referred to as a "tubular stent."

Furthermore, the stent of the present invention encompasses a stent prepared by braiding the tubular stent with wires made of metal or the like. The expression "braiding . . . with (e.g., braided with . . . )" means that wire-shaped strut portions (forming cells) of a stent and wires are braided alternately, so that the wires cross the strut portions alternately. In the present invention, a stent prepared by braiding a tubular stent with wires is referred to as a hybrid stent. Wires to be used herein can be produced using the above materials for stents. Preferably, nickel titanium (Ni—Ti alloy) is used. Also, a polymer made of resin can also be used, for example. The wire material and the material of a stent to be braided with the wires may be the same or different. The cross section of a wire is not limited. Wires with various cross sections such as a circle cross section, a substantially circular cross section, a polygonal cross section, and a substantially polygonal cross section can be used. The diameter of a wire to be used herein ranges from, when the cross section of the wire is circle, 4 μm to 100 μm and preferably ranges from 10 μm to 50 μm.

A tubular stent is braided with wires as follows. Wires and cell-forming stent strut portions are alternately braided, so that the wires cross the strut portions alternately, as described above. Here, the expression " . . . braided alternately with . . . so that . . . cross . . . alternately" means that, as shown in FIGS. 29A and B, wires and stent struts are braided so that each wire extends zig-zag or extends above its adjacent stent strut and then extends below the next adjacent stent strut, and so on. In this manner, wires cross stent struts alternately. A wire is inserted into one cell from the outside of the stent and then the wire is guided to move outside from the inside of the stent via the adjacent cell. Through repetition of this procedure, wires and stent strut portions can be alternately braided so that the wires cross the stent strut portions alternately. Braiding can be performed so that wires extend obliquely with respect to the longitudinal direction of the stent (that is, wires extend in both longitudinal and circumferential directions, as shown in FIGS. 26A and B, for example). In this case, when a wire reaches about half the width of the stent, the wire is folded back, braided, and then folded back, and so on. Through repetition of this procedure, wires and stent struts are braided so that the wires extend zig-zag with respect to the longitudinal direction. Also, wires and stent struts may be braided without folding back, so that the wires extend spirally with respect to the longitudinal direction of the stent. Preferably, braiding with a plurality of wires may be performed so that they are substantially parallel to each other. The number of wires to be braided ranges from, but is not limited to, 1 to 20, preferably ranges from 5 to 10, and is further preferably 8. In this case, a plurality of wires may be uniformly braided, so that the distances between wires are almost the same. The number of wires to be braided and the wire length can be appropriately determined depending on the size of a stent to be used herein. Finally, as shown in FIG. 26B, the whole circumference of a stent is braided with wires. Specifically, a portion near the center of the stent, accounting for ⅓ to ¾, and preferably ½ to ⅔ the full-length of the stent is braided with wires. In addition, the figure merely shows an example of the hybrid stent of the present invention. The hybrid stent of the present invention is not limited to such a stent having the structure shown in the figure. Also, when a stent is inserted into a bent part of a blood vessel, the stent is bent to fit the shape of the blood vessel. If wires braided with stent struts are fixed, such a structure prevents the stent from being bent (even when it is bent), so as to inhibit the flexibility of the stent. In the hybrid stent of the present invention, braided wires are not fixed to stent struts, so that the wires can slide and thus are movable between struts.

A tubular stent is braided with wires, so that the total surface area of the stent struts and the wires is larger than the surface area of the struts alone, and the gaps between cells of the stent become narrower. When the stent is placed in an affected area where aneurysm is present, the stent can interrupt blood flow into aneurysm and thus can prevent the rupture of aneurysm. Specifically, the hybrid stent of the present invention is a stent having a reinforced function of blocking blood flow while retaining the flexibility of the tubular stent. As a result, the stent can make it possible to more effectively prevent the rupture of aneurysm. Meanwhile, thin and very flexible wires are used herein, so that the flexibility of the whole stent is not lowered. Specifically, the hybrid stent of the present invention can be effectively used for treating aneurysm or thrombosis while retaining its good flexibility, and thus can prevent the restenosis of blood vessels.

In the hybrid stent braided with wires, the wires and stent struts are braided, so that the wires cross alternately the stent struts. Hence, the wires will never protrude outside the periphery of the stent to cause shortening.

FIG. 26A shows projection drawings of a tubular stent and FIG. 26B shows projection drawings of a hybrid stent wherein wires and stent struts are braided. FIG. 27A shows a projection drawing of a tubular stent and FIG. 27B shows a projection drawing of a hybrid stent wherein wires and stent struts are braided.

The hybrid stent is designed using CAD (computer aided design system) as shown on the left in FIG. 26B. The stent may be braided with wires manually or using an automatic braiding machine based on the design. A photograph showing a hybrid stent prepared based on the design is shown on the right in FIG. 26B. Wires themselves are thin and have elasticity and flexibility. Hence, wires overlap with each other because of their own rigidity and tension. Therefore, the braiding pattern of wires in an actually prepared hybrid stent does not completely match the pattern shown in a design drawing, but a stent with a pattern topologically analogous to that shown in the design drawing can be prepared.

Also, the stent of the present invention may contain an agent. Here the expression "the stent may contain an agent" means that the stent carries the agent so that the stent can release the agent and the agent can be eluted. Such an agent is not limited and a biologically active substance can be used, for example. Examples of a biologically active substance include an agent suppressing intimal thickening, an anticancer agent, an immunosuppressive agent, an antibiotic, an antirheumatic drug, an antithrombotic drug, an HMG-CoA reductase inhibitor, an ACE inhibitor, a calcium antagonist, an antihyperlipidemic agent, an antiinflammatory agent, an integrin inhibitor, an antiallergic agent, an antioxidant, a GPIIbIIIa antagonist, retinoid, flavonoid, carotenoid, a lipid improving drug, a DNA synthesis inhibitor, a tyrosine kinase inhibitor, an anti-platelet agent, a vascular smooth muscle growth inhibitor, an antiinflammatory drug, and an interferon. A plurality of these agents can also be used in combination. In particular, an intimal thickening-suppressing agent that prevents restenosis is preferable. An example of such an agent suppressing intimal thickening is an agent having effects of suppressing initimal thickening of blood vessels without inhibiting the growth of endothelial cells. Examples of such an agent include Argatroban ((2R,4R)-4-methyl-1-[N2-((RS)-3-methyl-1,2,3,4-tetrahydro-8-quinolinesulfonyl)-L-arginyl]-2-piperidinecarboxylic acid (JP Patent Publication (Kokai) No. 2001-190687 A; International Patent Publication WO2007/058190 pamphlet)), Ximelagatran, Melagatoran, Dabigatran, Dabigatran etexilate, Rapamycin, Everolimus, Biolimus A9, Zotarolimus, Tacrolimus, Paclitaxel, and statin.

An agent can be contained in a stent by coating the surface of a stent with an agent, for example. At this time, the surface of a stent may be directly coated with an agent or the surface of a stent may be coated with a polymer containing an agent. Also, a groove, a hole part, or the like is provided as a reservoir on a stent for storing an agent, and then an agent or a mixture of an agent and a polymer may be stored in the reservoir. A reservoir for storing an agent is as described in JP Patent Publication (Kohyo) No. 2009-524501 A, for example. Examples of a polymer to be used herein include flexible polymers having glass transition temperatures (Tg) ranging from −100° C. to 50° C., such as silicone rubber, urethane rubber, fluorocarbon polymer, polybutyl acrylate, polybutyl methacrylate, acryl rubber, natural rubber, an ethylene-vinyl acetate copolymer, a styrene-butadiene block copolymer, a styrene-isoprene block copolymer, and a styrene-isobuthylene block copolymer and biodegradable polymers such as polylactic acid, poly(lactic acid-glycolic acid), polyglycolic acid, poly(lactic acid-ϵ-caprolactone), poly(glycolic acid-trimethylene carbonate), and poly-β-hydroxybutyric acid. A polymer and an agent are mixed by dispersing the agent in the polymer, for example, according to International Patent Publication WO2009/031295 pamphlet. An agent contained in a stent is delivered to an affected area via a stent and then slowly released at the affected area.

Applications of Stent

The stent of the present invention is inserted, placed (deployed), and used in the inner cavity of an in vivo organ having a luminal structure. Examples of an in vivo luminal structure include a blood vessel, the trachea, the esophagus, the large intestines, the small intestines, the duodenum, urinary tracts, the urethra, and bile ducts. Examples of blood vessels include coronary arteries, peripheral blood vessels, carotid arteries, cerebral arteries, and veins.

The stent of the present invention can be inserted to be placed at a stricture of a coronary artery, for example, and then used for dilation of the coronary artery. Also, the stent is inserted to be placed at a site where aneurysm is formed, so that it can be used for preventing the rupture of aneurysm. In particular, for treatment of brain aneurysm that tends to be formed at a bent portion of a cerebral blood vessel, the stent is inserted to be placed at a bent portion of a blood vessel where the brain aneurysm is present, so as to decrease the blood flow within the brain aneurysm and to cause thrombogenesis. In this manner, the stent can be used for preventing the rupture of the brain aneurysm. Moreover, the stent is inserted to be placed for use in the stenosed trachea, esophagus, duodenum, large intestines, bile ducts, or the like (due to cancer), so that it can be used for expanding these tubular organs. Moreover, the stent can also be used as a matrix or reinforcement material for artificial blood vessels.

When a hybrid stent is prepared by braiding a tubular stent with wires, the area of strut portions of the stent is increased, having various new effects on the tubular stent. For example, such a hybrid stent can more effectively control the liquid flow in the in vivo tubular organ than a tubular stent. For example, the hybrid stent is inserted to be placed at a bent portion of a blood vessel where mass such as aneurysm or varix is present, so that it exerts more enhanced effects of decreasing the blood flow within the mass, causing thrombogenesis, and preventing the rupture of the mass.

The stent can be inserted into a tubular organ using a catheter. At this time, the stent is compressed to have a smaller outer diameter and then placed in a tubular organ. The stent can also be expanded using a balloon and then placed in a tubular organ. Specifically, the stent of the present invention may be a self-expansion or a balloon-expansion type.

Furthermore, the stent of the present invention contains an agent and the sustained release of the agent is possible. In such a manner, the stent can also be used as a drug delivery system.

The present invention will be described in more detail below with reference to examples. However, the present invention is not limited to the examples.

Example 1

Preparation of and Property Test for Tubular Stent

3DCAD Stent Model

In this example, a stent model having a closed-cell structure was designed on the basis of Pythagorean tessellation theory. This theory was employed because the mesh pattern of the stent having the closed-cell structure is composed so that it is filled with cells all having the same shape. According to the Pythagorean tessellation theory, the only geometrical shapes that can planarly fill a plane are quadrangles and hexagons (to be precise, triangles are also included).

A real-shape 3DCAD stent model was created using Solid Edge (SIEMENS PLM Software). Thereafter, the model was imported in IGES format into Pro/ENGINEER (Parametric Technology Corporation) and Rhinoceros (Robert McNeel & Associates) so that the surface model could be modified. A finite element model was then created with Marc. Mentat finite element software (MSC Software).

Mesh patterns with 3 types of closed cell structure were devised (FIG. 6). Firstly, the basic structure of the stent, a diamond-type pattern (pattern 0) was created. Secondly, an arrow tip type pattern (pattern A) was created. Thirdly, a pattern (pattern B) was created by rotating the arrow tip type pattern by 90°. These models are shown in FIG. 7. In the example, pattern A and pattern B were examined. This is because no bending and deformation could be achieved via application of load to some extent to the pattern 0 model, as revealed by the results of analysis.

Also, 3 stent models each were prepared for pattern A and pattern B, and then the following shape parameters were devised. The space between diagonal vertices of a stent cell: (b); the longitudinal length L of the stent cell: (h); and the width of the stent cell: (l) (FIG. 7 and FIGS. 8A and B).

Furthermore, the same number of stent cells and the same values for the parameters (h), (l), and the like were employed for pattern A and pattern B (FIG. 9). In addition, the shape variation of stent cells is expressed using nondimensional parameter S. Nondimensional parameters are represented by the following formulae for both pattern A and pattern B.

$$S_A = \frac{h}{L} \quad (1)$$

$$S_B = \frac{b}{\pi D} \quad (2)$$

Here, "L" denotes the longitudinal length of pattern A and "πD" denotes the distance in the circumferential direction of pattern B. In all stent models, the thickness and the width of the stent wire were determined to be 0.115 mm and 0.065 mm, respectively, and the outer diameter of the same was determined to be 5 mm.

Analysis Using Finite Element Method (FEM)

Large deformation elastic-plastic analyses were conducted using MSC Marc/Mentat versatile finite element method software (MSC Software, Santa Ana, Calif., U.S.A.), assuming that materials used herein were of an isotropically hardened plastic model.

Deformation Analysis Simulation of Stent (No. 1)

Bending Analysis of Stent

A stent for brain aneurysm is required to have a high degree of bending flexibility. This is because in the case of intracranial circulation composed of a complicated blood circulatory system, a stent is frequently placed at a site of a greatly curved blood vessel.

In this example, both deformation simulation by a finite element method and a bending test involving a mechanical experiment were performed for evaluation of the flexural rigidity of stents. The deformation simulation of stents will be described first.

To bend a stent for deformation in a deformation analysis simulation, an end part of a model was restrained, bending angle θ was given to the free end, and thus bending moment M required therefor was calculated. FIG. 12 is a model figure showing how the stent bending analysis was conducted. Bending moment M when the stent was rotated by angle θ was calculated (arrow with broken line). The bending angle was determined to range from 0° to 90° with reference to the bending angle of cerebral blood vessels.

The above results of analysis for pattern A (models 1, 2, and 3) are shown in FIG. 13 and the same for pattern B (models 4, 5, and 6) are shown in FIG. 14.

As shown in FIG. 13, stent models 1 to 3 of pattern A showed similar mechanical behavior at all curvatures. Also, the all models of pattern A were found to undergo buckling at curvatures of around 0.06 $radmm^{-1}$, as shown in FIG. 15.

Also, as shown in FIG. 14, stent models 4 to 6 of pattern B showed different behaviors. Model 6 showed deformation with the highest degree of flexibility. This is because cells composing the stent pattern are wrapped around the stent in the circumferential direction (see the shape of model 6 in FIG. 8B). Hence, the stent shows mechanical behavior partially analogous to that of a winding spring. Furthermore, deformed shapes of models 4 to 6 were compared. Models other than model 6 were found to undergo buckling as shown in FIG. 16 and FIG. 17. FIG. 16 shows the results for stent model 4, FIG. 17 shows the results for stent model 5, and FIG. 18 shows the results for stent model 6.

FIG. 16 shows the deformation results obtained by numeric simulation and specifically shows stent model 4, which underwent buckling at a curvature of 0.06 $radmm^{-1}$.

FIG. 17 shows the deformation result obtained by numeric simulation and specifically shows stent model 5, which underwent buckling at a curvature of 0.1 $radmm^{-1}$.

FIG. 18 shows the deformation result obtained by numeric simulation and specifically shows stent model 6, which underwent buckling at a curvature of 0.14 $radmm^{-1}$.

Deformation Analysis Simulation of Stent (No. 2)

Compression Analysis of Stent

A stent is placed within a blood vessel while being expanded. Thus, the force to be applied by the stent to the blood vessel wall is a very important mechanical element. To examine the expansive force of stents in this example, a stent was compressed by radially applying external pressure to the stent, so as to examine the extent to which the cross-sectional diameter could be shortened in the radial direction.

To radially compress a stent in this analysis, a part of a model was restrained, pressure was applied to the outer surface of the stent to 0.04 MPa, and the resulting amount of displacement in the radial direction was calculated. FIG. 19 is a model figure showing how the compression analysis of the stent was conducted. As shown on the left in FIG. 19, a displacement constraint was applied partially to the lower portion of a stent and pressure was thus applied to the outer surface of the stent, so that the stent was compressed in the radial direction (arrow with broken line).

Mechanical Test for Stent

Stent samples were actually prepared to experimentally confirm the validity of the results of numeric simulation in this experiment. At this time, one type (model 2) of pattern A stent sample was prepared and 3 types (models 4, 5, and 6) of pattern B stent sample were prepared. Here, regarding pattern A, all models had almost the same mechanical properties, as revealed by numerical analyses, so that only 1 pattern A model was processed.

Experimental conditions were employed with reference to the boundary conditions employed for stents subjected to the FEM analysis described above.

In this experiment, 4 types of stent sample were prepared by laser cutting, and they were used for a mechanical test (FIG. 20). A stent processor, Microworx Stent (LTT APPLIKATION, Germany), was used for laser cutting. All stent samples were composed of Ni—Ti tubes, and the diameter, length, thickness, and wire width of the tubes were 5.0 mm, 20 mm, 0.115 mm, and 0.065 mm, respectively. These were always 7 cells in the longitudinal direction and 8 cells in the circumferential direction.

For comparison of mechanical properties with the thus prepared stents having closed cell structures, a highly flexible Neuroform Stent 3 (Neuroform Micro delivery Stent System, Boston Scientific/, Fremont, Calif.) having an open cell structure that is used for the treatment of cerebral blood vessels was used. All stent samples were composed of Ni—Ti tubes, and the diameter, length, thickness, and wire width of the tubes were 5.0 mm, 20 mm, 0.115 mm, and 0.065 mm, respectively. These were always 7 cells in the longitudinal direction and 8 cells in the circumferential direction.

Bending Test for Stent

A bending test machine was produced for measuring the longitudinal flexural rigidity of stents (FIG. 21). FIG. 21A shows how the bending test was conducted using the bending test machine. FIG. 21B shows the state of a stent during experiment. An end part of a stent was completely fixed to bend the stent. Furthermore, a thin plastic pipe was inserted from the opposite end part into the lumen at a site 3.8 mm from the end and then a hook connected to a rod of a load cell (Kyowa Electronic Instruments Co., Ltd. Japan) was brought into contact with the pipe. When the load cell (on which a micrometer has been loaded) moves, the pipe is subjected to displacement, and thus the stent is bent. Deformation behavior observed at this time was captured with a digital camera E990 (CooLPix990; Nikon Tokyo, Japan), and then the curvature was calculated from the thus obtained image. Bending moment was calculated from stent length “L” and value “F” for the load cell at such time.

FIG. 22 shows the results obtained by the bending test. FIG. 22 is a graph showing the relationship among models 2, 4, 5, and 6, the bending moment of Neuroform Stent 3, and curvature. As shown in FIG. 22, the stent model 6 sample was found to have the lowest degree of flexural rigidity and the highest degree of flexibility among the stent samples prepared in this example. The stent model 6 sample was also found to exhibit mechanical behavior relatively similar to that exhibited by Neuroform Stent 3, which has an open cell structure and is actually used for treatment of cerebral blood vessels. Here, the difference in mechanical behavior between the two is a result of the following. Although the thickness of the metal tube to be used in the Neuroform Stent 3 was as thin as 60 μM, the thickness of the tube used for stent processing in this example was 115 μm, which was almost twice of the same figure for Neuroform. Stent rigidity was significantly affected by the thickness of the metal tube to be used for processing, indicating that the thicker the tube, the higher the rigidity.

It was revealed by numerical analysis that when stent model 6 obtained in this example has the same thickness (60 μm) as the Neuroform Stent, stent model 6 would have mechanical properties almost equivalent to those of Neuroform. Accordingly, it was concluded that even model 6 of such a pattern having a closed cell structure is able to exhibit a high degree of mechanical flexibility equivalent to or higher than that of a stent model having an open cell structure through examination of the use of a thin tube, thinner stent wires, soft materials, and the like.

In this example, not only values to be loaded upon deformation of stents, but also the deformed shapes were compared, and thus the models were examined for their effectiveness.

A stent to be used for cerebral blood vessels is placed in a largely curved or bent intracranial blood vessel, and thus the stent is bent to a greater degree than a stent to be used for coronary arteries or carotid arteries. In this example, a clinically used stent and stent model 6 having the highest degrees of flexibility among the stents examined in the example were bent to a bending angle of 180°, and then the deformed shapes were compared. FIG. 23 shows the deformed shapes of the stent model 6 sample (FIG. 23A) (pattern B, model 6) prepared in this example and the stent (FIG. 23B) (Neuroform Stent 3) that is actually clinically used, after they had been bent by 180° and thus deformed. As shown in FIG. 23, the stent sample prepared in this example was bent and deformed to result in uniform curvature. On the other hand, in the case of the deformed shape of Neuroform Stent 3, stent struts were found to protrude outside, and the cross-sectional area was found to decrease at a portion with a high curvature. Such a decrease poses the risk of damaging blood vessel walls. Also, a decrease in the cross-sectional area of the inner cavity of a stent can inhibit intravascular blood flow so as to induce thrombogenesis, and thus it is very hazardous.

As described above, it was possible to devise a stent model that has low flexural rigidity and a high degree of flexibility despite its closed cell structure by varying the shapes of cells composing the stent.

Compression Test for Stent

A compression test machine was produced for measuring the radial rigidity of stents (FIG. 24). FIG. 24A shows the whole compression test machine and FIG. 24B shows parts of the compression test machine. Radial rigidity was measured using a thin polyethylene film (Tetoron (trademark) film; Teijin DuPont Films Ltd. Japan) having a high degree of flexibility. The film was wrapped around a stent and the stent was compressed using a roller, so as to perform radial displacement. When the load cell (on which a micrometer had been loaded) moved, the film connected thereto was stretched, and then the load value at such time was measured.

The results are shown in FIG. 25. In FIG. 25, the horizontal axis represents the distance along which the film was stretched when the film had been wrapped around a stent and the stent had then been compressed, and the longitudinal axis represents the force required at such time. In the graph shown in FIG. 25, the lower the degree of radial rigidity (that is, the higher the degree of radial flexibility), the lower the position in the graph. As shown in FIG. 25, the stent model 6 was found to have the highest degree of radial flexibility of all the stents examined in the experiment.

Example 2

Preparation of and Property Test for Hybrid Stent Braided with Wires

The tubular stent model 6 in Example 1 was braided with wires. The stent was composed of an Ni—Ti tube and the diameter, length, thickness, and wire width of the tube were 5.0 mm, 20 mm, 0.115 mm, and 0.065 mm, respectively. These were 7 cells in the longitudinal direction and 8 cells in the circumferential direction. Wire made of a nickel titanium alloy having a diameter of 39 μm and a length of 30 cm was used. As shown in FIG. 29, a wire was inserted into a cell (which is located near the center of the stent in the longitudinal direction) from the outside to the inside of the stent and then the wire was guided to move outside from the inside of the stent via the adjacent cell so that it crossed the strut forming the cell. Through repetition of this procedure, the stent was braided with wires so that the wires crossed the stent struts alternately. At such time, braiding was performed so that wires obliquely extended with respect to the circumferential direction of the stent (that is, the wires were wrapped around the circumference of the stent). When the wires reached about half the width of the stent, the wires were folded back, following which they were braided in a direction that was the opposite of the initial direction (with respect to circumferential direction). Braiding with wires was continued until the wires returned about half the width of the stent and then the wires were folded back again. Braiding was continued until the wires reached about half the width of the stent. Both ends of a wire were bent inward so as to prevent it from protruding outside the stent. Similar procedures were performed for 8 wires as shown in FIG. 28B. The finally obtained stent is as shown in FIG. 26B (perspective drawing) and FIG. 27B (oblique perspective view). As shown in these figures, the stent was braided with wires near the center with respect to the longitudinal direction of the stent. Wires extended zig-zag in the longitudinal direction of the stent for a predetermined distance. The length of the stent portion braided with wires was about ½ the length of the whole stent.

When a hybrid stent was prepared, as shown on the left in FIG. 26B, the pattern structure of struts and wires of a hybrid stent prepared by braiding a tubular stent with wires was designed using a CAD (computer aided design) system. Then braiding was manually performed according to the design drawing.

A bending test was performed for the thus obtained hybrid stent using the bending test machine shown in FIG. 21. The results are shown in FIG. 30. FIG. 30 shows the results for the hybrid stent prepared in this example, tubular stents (models 2-6), and Neuroform 3.

As shown in FIG. 30, the hybrid stent was found to have flexural rigidity (flexibility) equivalent to that of the tubular stent model 6 and that of Neuroform 3.

EXPLANATION OF SYMBOLS

1 Side 1
2 Side 2
3 Side 3
4 Closed cells I
5 Closed cells II
6 Stent
7 Micrometer1
8 Micrometer2
9 Roller
10 Yarn
11 Load cell
12 PET film loop

INDUSTRIAL APPLICABILITY

The stent having a closed cell structure of the present invention can be safely used without allowing a part of wires to protrude inside or outside the stent, as in the cases of conventional stents having open cell structures. Also, the mesh pattern of the stent of the present invention is characterized in that all closed cells circumferentially adjacent to each other are congruent and similar in shape. Because of these characteristics, the density of closed cells (mesh density) forming the mesh pattern of the wall of the stent can be freely designed, and the stent can fit various in vivo tubular organs. Moreover, in the mesh pattern of the stent of the present invention, a single closed cell unit is characterized in that it has a point-symmetric substantially concave and substantially parallel hexagonal shape such that the interior angles at 2 vertices (of 6 vertices) between which other 2 vertices are located are each greater than 180°. Because of these characteristics, the present invention has good flexibility.

Furthermore, a hybrid stent prepared by braiding a tubular stent with wires can interrupt blood flow into the mass of an aortic aneurysm while good flexibility is retained, and thus rupture of the mass due to blood inflow can be prevented.

The invention claimed is:

1. A flexible cylinder-shaped stent to be inserted to be placed and used in the inner cavity of an in vivo tubular organ, which is bent and deformed to result in uniform curvature, wherein:

(i) the wall of the stent has a planar mesh pattern filled with a plurality of closed cells being adjacent to each other and having congruent shapes;
(ii) the closed cells have point-symmetric and concave and parallel hexagonal shapes;
(iii) all closed cells circumferentially adjacent to each other are congruent and similar in shape;
(iv) two closed cells adjacent to each other sharing different sides form a substantially V-shaped member; and
(v) the vertex of a folded part of the substantially V-shaped member points to the circumferential direction;
(vi) when substantially concave hexagon P is represented by vertices p1, p2, p3, p4, p5, and p6,
side p1p2 (side 1) and side p4p5 (side 1) are substantially the same in length and substantially parallel to each other,
side p2p3 (side 2) and side p5p6 (side 2) are substantially the same in length and substantially parallel to each other,
side p3p4 (side 3) and side p6p1 (side 3) are substantially the same in length and substantially parallel to each other, and
the interior angles at vertex p1 and vertex p4 are each greater than 180°;
(vii) when the outer diameter of the stent is determined to be "D" and the distance between vertex p6 and p3 that are each located between side 2 and side 3 of a single closed cell unit in the circumferential direction of the stent is denoted by "b", b/πD, in which πD indicates the outer circumferential length of the stent and is 0.25, and
wherein stent strut portions forming the cells of the stent are slidably braided with wires without fixing the wires to the stent, so as to enhance the function of interrupting blood flow while retaining flexibility and wherein:
a plurality of wires and stent struts are braided so that the wires alternately cross the stent struts;
the wires extend obliquely with respect to the longitudinal direction of the stent and when the wire reaches about half the width of the stent, the wire is folded back, braided, and then folded back, and through repetition of this procedure, wires and stent struts are braided so that the wires extend zig-zag with respect to the longitudinal direction; and a stent portion near the center of the stent accounting for a third (⅓) or more of the longitudinal length of the stent, is braided with wires.

2. The stent according to claim 1, wherein some of the 6 sides of each closed cell having a substantially concave hexagonal shape are arc-like.

3. The stent according to claim 2, wherein side p2p3 (side 2), side p3p4 (side 3), side p5p6 (side 2), and side p6p1 (side 3) are arc-like.

4. The stent according to claim 1, which is formed using titanium, nickel, stainless steel, platinum, gold, silver, copper, iron, chromium, cobalt, aluminium, molybdenum, manganese, tantalum, tungsten, niobium, magnesium, calcium, an alloy containing any thereof, or a synthetic resin as a material.

5. The stent according to claim 4, which is formed using a biodegradable polymer as a material.

6. The stent according to claim 1, which carries an agent so that the agent can be eluted.

7. The stent according to claim 6, wherein the agent is selected from the group consisting of an intimal-thickening suppressing agent, an anticancer agent, an immunosuppressive agent, an antibiotic, an antirheumatic drug, an antithrombotic drug, an HMG-CoA reductase inhibitor, an ACE inhibitor, a calcium antagonist, an antihyperlipidemic agent, an antiinflammatory agent, an integrin inhibitor, an antiallergic agent, an antioxidant, a GPIIbIIIa antagonist, retinoid, flavonoid, carotenoid, a lipid improving drug, a DNA synthesis inhibitor, a tyrosine kinase inhibitor, an anti-platelet agent, a vascular smooth muscle growth inhibitor, an antiinflammatory drug, and interferon.

8. The stent according to claim 1, wherein the in vivo tubular organ is selected from the group consisting of a blood vessel, the trachea, the esophagus, the large intestines, the small intestines, the duodenum, urinary tracts, the urethra, and bile ducts.

9. The stent according to claim 8, wherein the in vivo tubular organ is a cerebral blood vessel.

10. The stent according to claim 1, wherein 4 to 20 closed cells are longitudinally present adjacent to each other and 4 to 36 closed cells are circumferentially present adjacent to each other.

* * * * *